US007632658B2

(12) United States Patent
Joly

(10) Patent No.: US 7,632,658 B2
(45) Date of Patent: Dec. 15, 2009

(54) METHOD OF USING AMINOPEPTIDASE TO PRODUCE CLEAVED POLYPEPTIDES

(75) Inventor: John C. Joly, San Mateo, CA (US)

(73) Assignee: Genentech, Inc., South San Francisco ( * ) Notice: Subject to any disclaimer, the term of this patent is extended or adjusted under 35 U.S.C. 154(b) by 290 days.

(21) Appl. No.: 11/741,510

(22) Filed: Apr. 27, 2007

(65) Prior Publication Data

US 2008/0160572 A1    Jul. 3, 2008

Related U.S. Application Data

(62) Division of application No. 11/131,035, filed on May 16, 2005, now Pat. No. 7,229,787, which is a division of application No. 10/243,789, filed on Sep. 12, 2002, now Pat. No. 6,921,659.

(60) Provisional application No. 60/322,350, filed on Sep. 13, 2001.

(51) Int. Cl.
*C12P 21/06* (2006.01)
(52) U.S. Cl. .................................... 435/68.1
(58) Field of Classification Search ................ None
See application file for complete search history.

(56) References Cited

U.S. PATENT DOCUMENTS

| | | | |
|---|---|---|---|
| 4,865,974 | A | 9/1989 | Ben-Bassat et al. |
| 4,946,783 | A | 8/1990 | Beckwith et al. |
| 5,304,472 | A | 4/1994 | Bass et al. |
| 5,508,192 | A | 4/1996 | Georgiou et al. |
| 5,639,635 | A | 6/1997 | Joly et al. |
| 5,789,199 | A | 8/1998 | Joly et al. |
| 6,127,144 | A | 10/2000 | Bartfeld et al. |
| 6,428,997 | B1 | 8/2002 | Lee et al. |

FOREIGN PATENT DOCUMENTS

| | | |
|---|---|---|
| EP | 0 489 711 | 10/2003 |
| KR | 2002044601 | 6/2002 |
| WO | WO 86/01229 | 2/1986 |
| WO | WO 88/05821 | 8/1988 |
| WO | 94/12636 | 9/1994 |
| WO | WO 00/34452 | 6/2000 |
| WO | WO 00/66761 | 11/2000 |
| WO | WO 03/023030 A3 | 3/2003 |

OTHER PUBLICATIONS

Aminopeptidase, definition from Dorland's Medical Dictionary (2007).*
Alberts et al., "Normal Genes can be Easily Replaced by Mutant Ones in Bacteria and Some Lower Eucaryotes" *Molecular Biology of the Cell*, 3rd edition, New York:Garland Publishing, Inc. pp. 325-326 (1994).
Andersen et al., "Metabolic Oscillations in an *E. coli* Fermentation." *Biotechnol. Bioeng*. 75 (2):212-218 (Oct. 2001).
Ausubel et al., "Chapter 16: Protein Expression" *Current Protocols in Molecular Biology (Online)*, John Wiley & Sons, Inc. (2002).
Bachmann., "Derivations and Genotypes of Some Mutant Derivatives of *Escherichia coli* K-12." *Escherichia coli and Salmonella typhimurium: Cellular and Molecular Biology*. (Washington, DC: American Society for Microbiology.), Chapter 72, 2:1190-1219 (1987).
Bachmann., "Pedigrees of Some Mutant Strains of *Escherichia coli* K-12." *Bact. Rev*. 36(4):525-557 (Dec. 1972).
Baneyx and Georgiou., "Expression of Proteolytically Sensitive Polypeptides in *Escherichia coli*." *Stability of Protein Pharmaceuticals*., Ahern and Manning, eds., NY:Plenum Press, Chapter 3, pp. 69-108 (1992).
Ben-Bassat et al., "Processing of the Initiation Methionine from Proteins: Properties of the *Escherichia coli* Methionine Aminopeptidase and its Gene Structure" *Journal of Bacteriology* 169(2):751-757 (1987).
Blattner et al., "The Complete Genome of *Escherichia coli* K-12" *Science* (Database SwissProt on GenCore, Compugen, Ltd. GenBank, Gene Sequence) 277:1453-1474 (Sep. 1997).
Blattner at al., "The Complete Genome Sequence of *Escherichia coli* K-12." *Science* 277:1453-1462 (Sep. 1997).
Blattner, F.R. et al., "The complete genome sequence of *Escherichia coli* K-12" NCBI Database (Acc. No. AE000321; XP-002368679) (Dec. 1, 2000).
Blattner, F.R., et al., "The complete genome sequence os *Escherichia coli* K-12" NCBI Database (Acc. No. AAC75384; XP-002368680) (Dec. 1, 2000).
Bujnicki, J. M. et al., "Identification of a bifunctional enzyme MnmC involved in the biosynthesis of a hypermodified uridine in the wobble position of tRNA" *RNA*, Cold Spring Harbor Laboratory Press vol. 10(8):1236-1242 (2004).
Chang et al., "High-Level Secretion of Human Growth Hormone by *Escherichia coli*" *Gene* 55:189-196 (1987).
Chaudhury and Smith., "*Escherichia coli* recBC Deletion Mutants." *J. Bacteriol*. 160(2):788-791 (Nov. 1984).
Elish et al., "Biochemical Analysis of Spontaneous fepA Mutants of *Escherichia coli*." *J. Gen. Microbiol*. 134:1355-1364 (1988).
Fowler, E., et al., "Removal of N-Terminal Blocking Groups from Proteins" *Current Protocols in Protein Science*Supplement 3:11.7.1 (1996).

(Continued)

*Primary Examiner*—Sheridan Swope
(74) *Attorney, Agent, or Firm*—Craig G. Svoboda; Genentech, Inc.

(57) ABSTRACT

A gram-negative bacterial cell is described that is deficient in a chromosomal gene present in a wild-type such cell which gene shares at least 80% sequence identity with the native sequence of the yfcK gene and encodes an aminopeptidase. Alternatively, a gram-negative bacterial cell is deficient in a chromosomal gene present in a wild-type such cell which gene encodes an aminopeptidase that shares at least 80% sequence identity with the native sequence of aminopeptidase b2324. Either of these types of cells, when comprising a nucleic acid encoding a heterologous polypeptide, produces an N-terminal unclipped polypeptide when it is cultured and the polypeptide recovered, with virtually no N-terminal clipped polypeptide produced as an impurity. Conversely, a method is provided for cleaving an N-terminal amino acid from a polypeptide comprising contacting the polypeptide with an aminopeptidase sharing at least 80% sequence identity with the native sequence of aminopeptidase b2324.

19 Claims, 5 Drawing Sheets

OTHER PUBLICATIONS

Gonzales and Robert-Baudouy., "Bacterial Aminopeptidases: Properties and Functions." *FEMS Microbiology Reviews* 18(4):319-344 (1996).

Joly et al., "Overexpression of *Escherichia coli* Oxidoreductases Increases Recombinant Insulin-Like Growth Factor-I Accumulation" *Proc. Natl. Acad. Sci. USA* 95:2773-2777 (Mar. 1998).

Kleckner et al., "Genetic Engineering in Vivo Using Translocatable Drug-Resistance Elements: New Methods in Bacterial Genetics." *J. Mol. Biol.* 116:125-159 (1977).

Knappik et al., "The Effect of Folding Catalysts on the In Vivo Folding Process of Different Antibody Fragments Expressed in *Escherichia coli*" *Bio/Technology* 11:77-83 (Jan. 1993).

Lawther et al., "Molecular Basis of Valine Resistance in *Escherichia coli* K-12." *Proc. Natl. Acad. Sci. USA* 78:922-925 (Feb. 1981).

Mark et al., "Genetic Mapping of trxA, a Gene Affecting Thioredoxin in *Escherichia coli* K12." *Mol. Gen. Genet.* 155:145-152 (1977).

Metcalf et al., "Use of the rep Technique for Allele Replacement to Construct New *Escherichia coli* Hosts for Maintenance of R6Kγ Origin Plasmids at Different Copy Numbers." *Gene.* 138:1-7 (1994).

Miller, Charles G., "Protein Degradation and Proteolytic Modification." *Escherichia coli and Salmonella.*, Frederick C. Neidhardt, ASM Press, Chapter 62, pp. 938-954 (1996).

Park et al., "Secretory Production of Recombinant Protein by a High Cell Density Culture of a Protease Negative Mutant *Escherichia coli* Strain." *Biotechnol. Prog.* 15:164-167 (1999).

Wulfing and Pluckthun, "Correctly Folded T-Cell Receptor Fragments in the Periplasm of *Escherichia coli*" *J. Mol. Biol.* 242:655-669 (1994).

Alison M. Griffen et al., "Protease-deficient mutants of the Quorn mycoprotein fungus, Fusarium graminearum A3/5" *FEMS Microbiology Letters* 158:231-236 (1998).

Hideki Yanagi eta l., "Reinforcement of Chaperone Function and Inhibition of Protein Degradation Activity" *Bioscience and Industry* 57(2):108-109 (1999).

Hiroyuki Horiuchi et al., "Utilization of Recombinant Filamentous Fungi for Protein Production" *Nippon Nogeikagaku Kaishi, Journal of Japan Society for Bioscience, Biotechnology and Agrochemistry* 67(6):965-968 (1993).

Isabelle Poquet et al., "Optimising the production of heterologous exported proteins in *Lactococcus lactis* by inactivation of HtrA, the unique housekeeping surface protease" *Dairy Science & Technology (EDP Sciences)* 81:37-47 ((abstract) 2001).

Johannes P.T.W. van den Hombergh et al., "*Aspergillus* as a host for heterologous protein production: the problem of proteases" *Trends Biotechnol.* 15(7):256-263 (1997).

Jonathan M. Wingfield et al., "Increased activity of a model heterologous protein in *Saccharomyces cerevisaia* strains with reduced vacuolar proteinases" *Applied Microbiology Biotechnology* 39(2):211-215 (May 1993).

M. Honjo et al., "Construction of a highly efficient host-vector system for secretion of heterologous protein in *Bacillus subtilis*" *Journal of Biotechnology* 6:191-204 (1987).

X.F. Zheng et al., "Construction of a low-serine-type-carboxypeptidase-producing mutant of *Aspergillus oryzae* by the expression of antisense RNA and its use as a host for heterologous protein secretion" *Appl Microbiol Biotechnol* 49:39-44 (1998).

Yoshihiro Yamamoto et al., "Construction of a Contiguous 874-kb Sequence of the *Escherichia coli* -K12 Genome Corresponding to 50.0-68.8 min on the Linkage Map and Analysis of Its Sequence Features" *DNA Research* 4(2):91-113 (1997).

Yoshio Furutani, "Secretion-Production of Heterogeneous Proteins in *Bacillus subtilis*" *Science of Life "Genetics"* Suppl. 1:27-35 (Mar. 1988).

* cited by examiner

1A1 W3110
⇓
1A2 W3110 ΔfhuA
⇓
7C1 W3110 ΔfhuA Δ(arg-F-lac)169 phoAΔE15
⇓
16C9 W3110 ΔfhuA Δ(arg-F-lac)169 phoAΔE15 deoC2
⇓
23E3 W3110 ΔfhuA Δ(arg-F-lac)169 phoAΔE15 deoC2 degP::kanR
⇓
33B6 W3110 ΔfhuA Δ(arg-F-lac)169 phoAΔE15 deoC2 degP::kanR ilvG2096
⇓
61G3 W3110 ΔfhuA Δ(arg-F-lac)169 phoAΔE15 deoC2 degP::kanR, ilvG2096 Δb2324

*FIG._1*

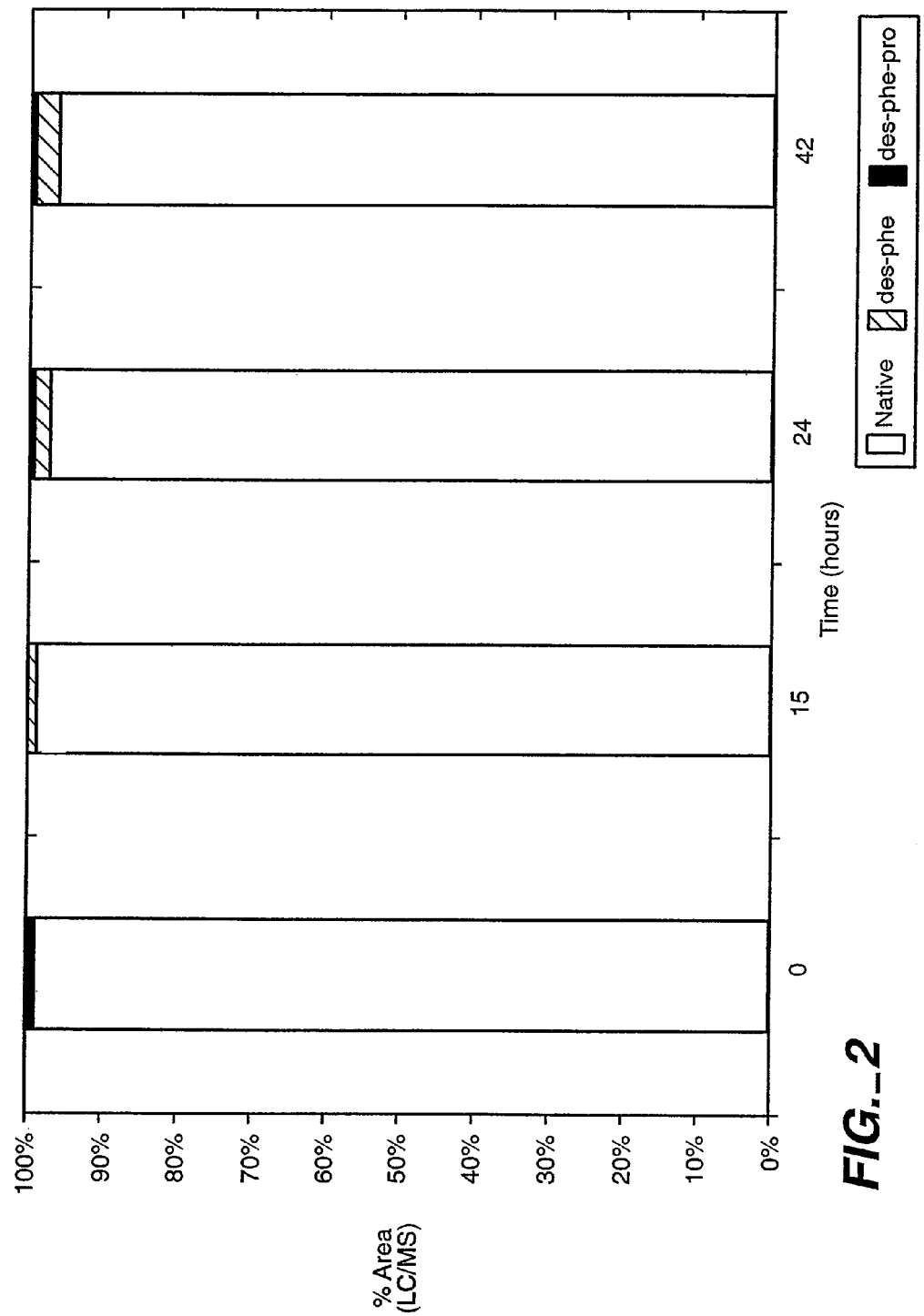
FIG._2

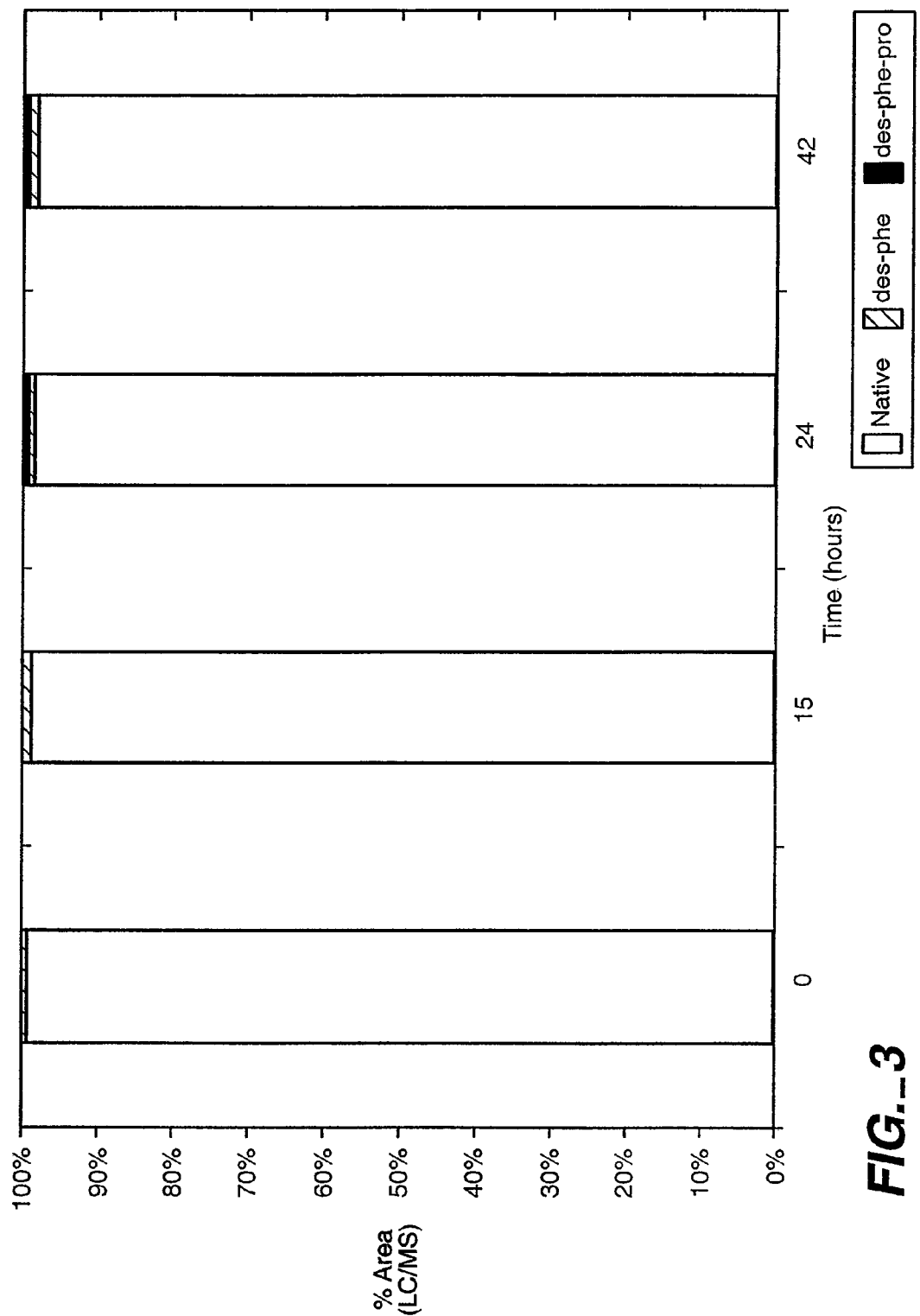
FIG._3

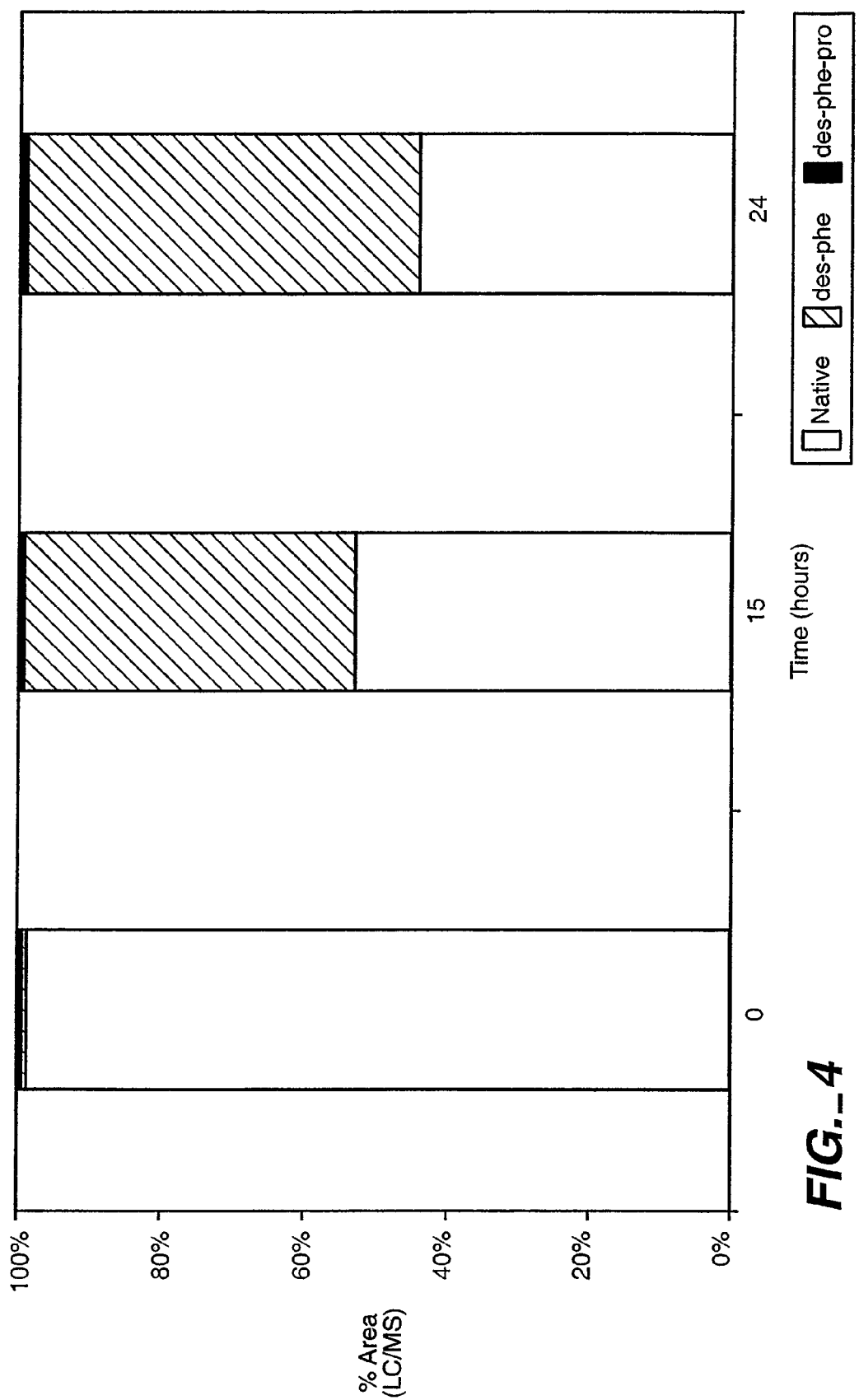
FIG._4

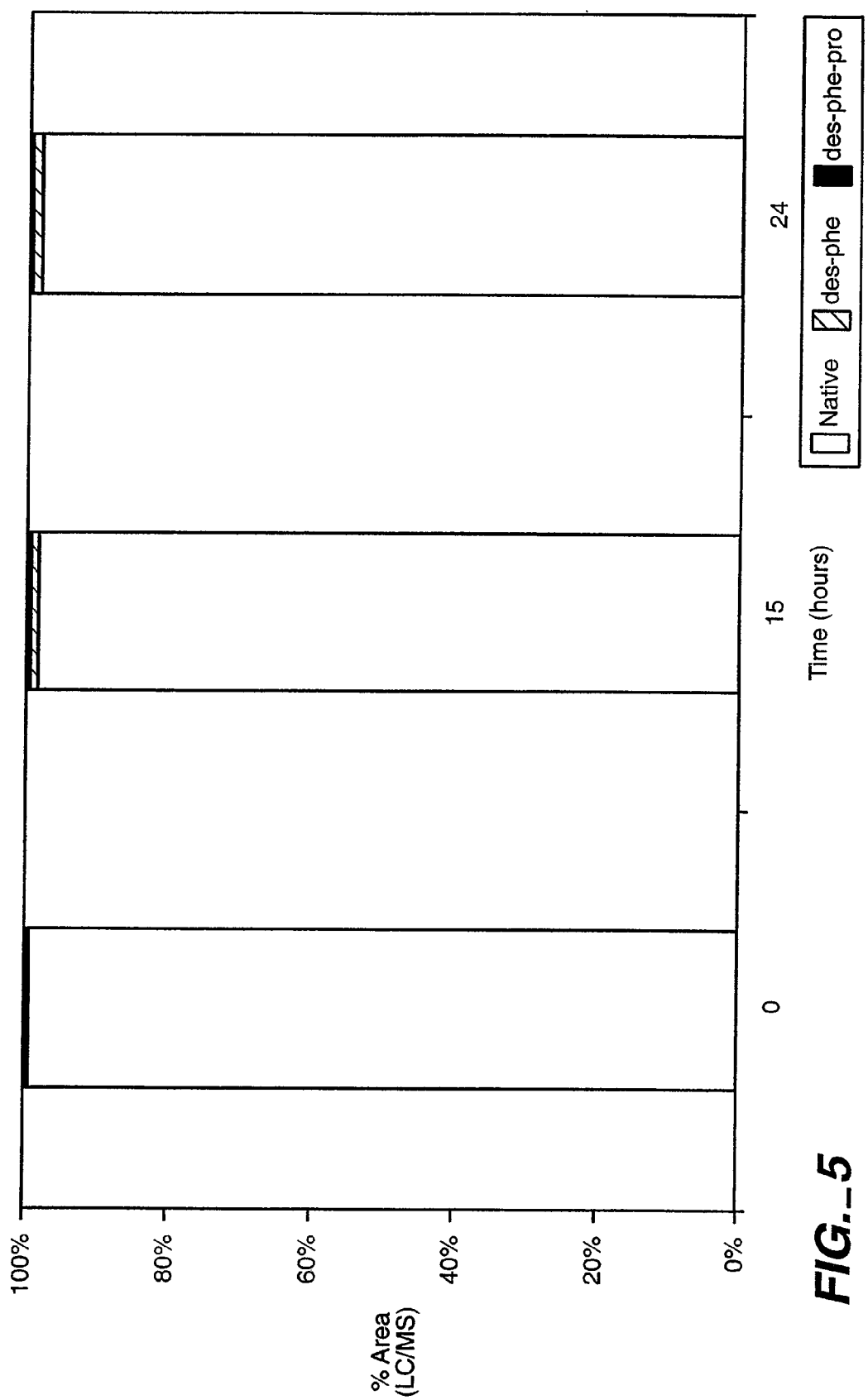
FIG._5

```
                         SEQUENCE LISTING

<160> NUMBER OF SEQ ID NOS: 2

<210> SEQ ID NO 1
<211> LENGTH: 2067
<212> TYPE: DNA
<213> ORGANISM: Escherichia coli

<400> SEQUENCE: 1
ttgcgcagcc ttacacacat cgctaagatc gagccaccgc ctgtaagacg           50
agtaacttac gtgaaacact actccataca acctgccaac ctcgaattta          100
atgctgaggg tacacctgtt tcccgagatt ttgacgatgt ctattttttcc         150 aacgataacg ggctggaaga gacgcgttat gttttctgg gaggcaacca           200 attagaggta cgctttcctg agcatccaca tcctctgttt gtggtagcag          250
agagcggctt cggcaccgga ttaaacttcc tgacgctatg gcaggcattt          300
gatcagtttc gcgaagcgca tccgcaagcg caattacaac gcttacattt          350
cattagtttt gagaaatttc ccctcacccg tgcggattta gccttagcgc          400
atcaacactg gccggaactg gctccgtggg cagaacaact tcaggcgcag          450
tggccaatgc ccttgcccgg ttgccatcgt ttattgctcg atgaaggccg          500
cgtgacgctg gatttatggt ttggcgatat taacgaactg accagccaac          550
tggacgattc gctaaatcaa aaagtagatg cctggtttct ggacggcttt          600
gcgccagcga aaaacccgga tatgtggacg caaaatctgt ttaacgccat          650
ggcaaggttg gcgcgtccgg gcggcacgct ggcgacattt acgtctgccg          700
gttttgtccg ccgcggtttg caggacgccg gattcacgat gcaaaaacgt          750
aagggctttg gcgcaaacg ggaaatgctt tgcggggtga tggaacagac           800
attaccgctc ccctgctccg cgccgtggtt taaccgcacg ggcagcagca          850
aacgggaagc ggcgattatc ggcggtggta ttgccagcgc gttgttgtcg          900
ctggcgctat tacggcgcgg ctggcaggta acgctttatt gcgcggatga          950
ggcccccgca ctgggtgctt ccggcaatcg ccaggggggcg ctgtatccgt         1000 tattaagcaa acacgatgag gcgctaaacc gcttttttctc taatgcgttt         1050 acttttgctc gtcggtttta cgaccaatta cccgttaaat ttgatcatga         1100
ctggtgcggc gtcacgcagt taggctggga tgagaaaagc cagcataaaa         1150
tcgcacagat gttgtcaatg gatttacccg cagaactggc tgtagccgtt         1200
gaggcaaatg cggttgaaca aattacgggc gttgcgacaa attgcagcgg         1250
cattacttat ccgcaaggtg gttggctgtg cccagcagaa ctgacccgta         1300
atgtgctgga actggcgcaa cagcagggtt tgcagattta ttatcaatat         1350
cagttacaga atttatcccg taaggatgac tgttggttgt tgaatttttgc         1400 aggagatcag caagcaacac acagcgtagt ggtactggcg aacgggcatc         1450
aaatcagccg attcagccaa acgtcgactc tcccggtgta ttcggttgcc         1500
gggcaggtca gccatattcc gacaacgccg gaattggcag agctgaagca         1550
ggtgctgtgc tatgacggtt atctcacgcc acaaaatccg gcgaatcaac         1600
```

```
atcattgtat tggtgccagt tatcatcgcg gcagcgaaga tacggcgtac      1650
agtgaggacg atcagcagca gaatcgccag cggttgattg attgtttccc      1700
gcaggcacag tgggcaaaag aggttgatgt cagtgataaa gaggcgcgct      1750
gcggtgtgcg ttgtgccacc cgcgatcatc tgccaatggt aggcaatgtt      1800
cccgattatg aggcaacact cgtggaatat cgtcgttgg cggagcagaa       1850 agatgaggcg gtaagcgcgc cggttttga cgatctcttt atgtttgcgg       1900
ctttaggttc tcgcggtttg tgttctgccc cgctgtgtgc cgagattctg      1950
gcggcgcaga tgagcgacga accgattccg atggatgcca gtacgctggc      2000
ggcgttaaac ccgaatcggt tatgggtgcg gaaattgttg aagggtaaag      2050
cggttaaggc ggggtaa                                          2067
```

<210> SEQ ID NO 2
<211> LENGTH: 688
<212> TYPE: PRT
<213> ORGANISM: Escherichia coli

<400> SEQUENCE: 2

```
Met Arg Ser Leu Thr His Ile Ala Lys Ile Glu Pro Pro Pro Val
  1               5                  10                  15

Arg Arg Val Thr Tyr Val Lys His Tyr Ser Ile Gln Pro Ala Asn
                 20                  25                  30

Leu Glu Phe Asn Ala Glu Gly Thr Pro Val Ser Arg Asp Phe Asp
             35                  40                  45

Asp Val Tyr Phe Ser Asn Asp Asn Gly Leu Glu Glu Thr Arg Tyr
         50                  55                  60

Val Phe Leu Gly Gly Asn Gln Leu Glu Val Arg Phe Pro Glu His
     65                  70                  75

Pro His Pro Leu Phe Val Val Ala Glu Ser Gly Phe Gly Thr Gly
             80                  85                  90

Leu Asn Phe Leu Thr Leu Trp Gln Ala Phe Asp Gln Phe Arg Glu
             95                 100                 105

Ala His Pro Gln Ala Gln Leu Gln Arg Leu His Phe Ile Ser Phe
            110                 115                 120

Glu Lys Phe Pro Leu Thr Arg Ala Asp Leu Ala Leu Ala His Gln
            125                 130                 135

His Trp Pro Glu Leu Ala Pro Trp Ala Glu Gln Leu Gln Ala Gln
            140                 145                 150

Trp Pro Met Pro Leu Pro Gly Cys His Arg Leu Leu Leu Asp Glu
            155                 160                 165

Gly Arg Val Thr Leu Asp Leu Trp Phe Gly Asp Ile Asn Glu Leu
            170                 175                 180

Thr Ser Gln Leu Asp Asp Ser Leu Asn Gln Lys Val Asp Ala Trp
            185                 190                 195

Phe Leu Asp Gly Phe Ala Pro Ala Lys Asn Pro Asp Met Trp Thr
            200                 205                 210

Gln Asn Leu Phe Asn Ala Met Ala Arg Leu Ala Arg Pro Gly Gly
            215                 220                 225

Thr Leu Ala Thr Phe Thr Ser Ala Gly Phe Val Arg Arg Gly Leu
            230                 235                 240

Gln Asp Ala Gly Phe Thr Met Gln Lys Arg Lys Gly Phe Gly Arg
            245                 250                 255
```

```
Lys Arg Glu Met Leu Cys Gly Val Met Glu Gln Thr Leu Pro Leu
            260                 265                 270

Pro Cys Ser Ala Pro Trp Phe Asn Arg Thr Gly Ser Ser Lys Arg
            275                 280                 285

Glu Ala Ala Ile Ile Gly Gly Gly Ile Ala Ser Ala Leu Leu Ser
            290                 295                 300

Leu Ala Leu Leu Arg Arg Gly Trp Gln Val Thr Leu Tyr Cys Ala
            305                 310                 315

Asp Glu Ala Pro Ala Leu Gly Ala Ser Gly Asn Arg Gln Gly Ala
            320                 325                 330

Leu Tyr Pro Leu Leu Ser Lys His Asp Glu Ala Leu Asn Arg Phe
            335                 340                 345

Phe Ser Asn Ala Phe Thr Phe Ala Arg Arg Phe Tyr Asp Gln Leu
            350                 355                 360

Pro Val Lys Phe Asp His Asp Trp Cys Gly Val Thr Gln Leu Gly
            365                 370                 375

Trp Asp Glu Lys Ser Gln His Lys Ile Ala Gln Met Leu Ser Met
            380                 385                 390

Asp Leu Pro Ala Glu Leu Ala Val Ala Val Glu Ala Asn Ala Val
            395                 400                 405

Glu Gln Ile Thr Gly Val Ala Thr Asn Cys Ser Gly Ile Thr Tyr
            410                 415                 420

Pro Gln Gly Gly Trp Leu Cys Pro Ala Glu Leu Thr Arg Asn Val
            425                 430                 435

Leu Glu Leu Ala Gln Gln Gly Leu Gln Ile Tyr Tyr Gln Tyr
            440                 445                 450

Gln Leu Gln Asn Leu Ser Arg Lys Asp Asp Cys Trp Leu Leu Asn
            455                 460                 465

Phe Ala Gly Asp Gln Gln Ala Thr His Ser Val Val Leu Ala
            470                 475                 480

Asn Gly His Gln Ile Ser Arg Phe Ser Gln Thr Ser Thr Leu Pro
            485                 490                 495

Val Tyr Ser Val Ala Gly Gln Val Ser His Ile Pro Thr Thr Pro
            500                 505                 510

Glu Leu Ala Glu Leu Lys Gln Val Leu Cys Tyr Asp Gly Tyr Leu
            515                 520                 525

Thr Pro Gln Asn Pro Ala Asn Gln His His Cys Ile Gly Ala Ser
            530                 535                 540

Tyr His Arg Gly Ser Glu Asp Thr Ala Tyr Ser Glu Asp Gln
            545                 550                 555

Gln Gln Asn Arg Gln Arg Leu Ile Asp Cys Phe Pro Gln Ala Gln
            560                 565                 570

Trp Ala Lys Glu Val Asp Val Ser Asp Lys Glu Ala Arg Cys Gly
            575                 580                 585

Val Arg Cys Ala Thr Arg Asp His Leu Pro Met Val Gly Asn Val
            590                 595                 600

Pro Asp Tyr Glu Ala Thr Leu Val Glu Tyr Ala Ser Leu Ala Glu
            605                 610                 615

Gln Lys Asp Glu Ala Val Ser Ala Pro Val Phe Asp Asp Leu Phe
            620                 625                 630

Met Phe Ala Ala Leu Gly Ser Arg Gly Leu Cys Ser Ala Pro Leu
            635                 640                 645
```

```
Cys Ala Glu Ile Leu Ala Ala Gln Met Ser Asp Glu Pro Ile Pro
                650                 655                 660

Met Asp Ala Ser Thr Leu Ala Ala Leu Asn Pro Asn Arg Leu Trp
                665                 670                 675

Val Arg Lys Leu Leu Lys Gly Lys Ala Val Lys Ala Gly
                680                 685
```

US 7,632,658 B2

METHOD OF USING AMINOPEPTIDASE TO PRODUCE CLEAVED POLYPEPTIDES

RELATED APPLICATIONS

This application is a divisional application of application Ser. No. 11/131,035 filed May 16, 2005, now U.S. Pat. No. 7,229,787, which is a divisional application of application Ser. No. 10/243,789 filed 12 Sep. 2002, now U.S. Pat. No. 6,921,659, which is a non-provisional application filed under 37 CFR 1.53(b)(1), claiming priority under 35 USC 119(e) to provisional application No. 60/322,350 filed Sep. 13, 2001, the contents of which are incorporated herein by reference.

BACKGROUND OF THE INVENTION

1. Field of the Invention

This invention relates to the discovery of new bacterial aminopeptidases. More particularly, the invention is directed to an important enzyme activity the deletion or overexpression of which from bacteria improves the respective recovery of uncleaved or cleaved polypeptides produced in the bacteria such as recombinant polypeptides.

2. Description of Related Art

Some proteins have their N-terminal amino acid residue clipped off when they are made in gram-negative bacteria and archaebacteria such as *E. coli* due to the presence of aminopeptidases in the cells. As a result, an impurity closely related to the wild-type polypeptide is introduced into the cell culture either simultaneously or upon subsequent cell lysis as part of the product purification process. This impurity must be removed from the wild-type polypeptide if therapeutically useful proteins are to be prepared. An example is human growth hormone (hGH), which has its N-terminal phenylalanine residue cleaved when made in *E. coli*. This variant form of hGH (des-phe hGH), produced upon cell lysis to form a mixture with the unclipped hGH (native hGH), is difficult to remove from the mixture. Such removal requires subjection of the mixture to hydrophobic interaction chromatography. It would be desirable to avoid this extra purification step.

Additionally, it is desired in some instances to obtain polypeptides with the N-terminal amino acid residue cleaved and to amplify the quantities of such polypeptides relative to the native-sequence counterpart to obtain purer cleaved material.

Several of the known *E. coli* aminopeptidases have broad specificity and can cleave a variety of residues at the N-terminus, e.g., pepA, pepB, and pepN (*Escherichia coli* and *Salmonella*, Frederick C. Neidhardt (Ed), ASM Press. Chapter 62 by Charles Miller-Protein Degradation and Proteolytic Modification, pp 938-954 (1996); Gonzales and Robert-Baudouy, *FEMS Microbiology Reviews*. 18 (4):319-44 (1996). The gene yfcK encoding b2324 found in the K12 strain of *E. coli* was listed as a "putative peptidase" by the *E. coli* genome sequencing project (Blattner et al., *Science*, 277: 1453-62 (1997)) in the GenBank database (accession number AE000321), but no further information on its enzyme activity is provided. The homolog in *E. coli* strain O157:H7 is identical to the yfcK gene in the K12 strain. There is a need in the art to identify bacterial aminopeptidases that can be manipulated to obtain purer uncleaved or cleaved polypeptides.

SUMMARY OF THE INVENTION

The enzyme b2324 encoded by yfcK has now been identified as an aminopeptidase, i.e., an enzyme responsible for clipping N-termini from polypeptides. Upon its identification, the present invention is as claimed.

In one embodiment, the genes encoding aminopeptidases homologous to this enzyme, including the yfcK gene encoding aminopeptidase b2324, are eliminated from gram-negative bacterial strains, as by genetic disruption of the chromosome, so that the clipped impurity is no longer produced to any significant degree. The additional purification step to remove the clipped impurity is thereby eliminated. At least one resulting strain has been found to produce unclipped polypeptide in equal amounts to the parent strains.

Specifically, a gram-negative bacterial cell is provided that is deficient in a chromosomal gene having at least an 80% sequence identity to (a) a DNA molecule encoding a native-sequence aminopeptidase b2324 having the sequence of amino acid residues from 1 to 688 of SEQ ID NO:2, or (b) the complement of the DNA molecule of (a), and encoding an aminopeptidase. The naturally occurring equivalent to such cells contains the chromosomal gene, but the cells of this invention represent a manipulation to the wild-type cell, generally through genetic means, but by any means available, to eliminate or disable such gene so that it will not encode an aminopeptidase.

Alternatively, the invention provides a gram-negative bacterial cell deficient in a chromosomal gene comprising (a) DNA encoding a polypeptide scoring at least 80% positives when compared to the sequence of amino acid residues from 1 to 688 of SEQ ID NO:2, or (b) the complement of the DNA of (a), said polypeptide being an aminopeptidase.

Still alternatively, the invention provides a gram-negative bacterial cell deficient in a chromosomal gene having at least an 80% sequence identity to native-sequence yfcK gene having the sequence of nucleotides from 1 to 2067 of SEQ ID NO:1 and encoding an aminopeptidase.

In another embodiment, an *E. coli* cell is provided that is deficient in the chromosomal native-sequence yfcK gene.

Preferably, such cells set forth above are deficient in at least one gene encoding a protease, for example, degP or fhuA. Additionally, such cells may comprise a nucleic acid encoding a polypeptide heterologous to the cell, preferably eukaryotic, more preferably mammalian, and most preferably human, such as human growth hormone.

In another embodiment, the invention provides a method for producing a heterologous polypeptide comprising (a) culturing the cells set forth above and (b) recovering the polypeptide from the cells. Preferably the culturing takes place in a fermentor. In another preferred embodiment, the polypeptide is recovered from the periplasm or culture medium of the cell. In a further preferred embodiment, the recovery is by cell disruption to form a lysate, and preferably intact polypeptide is purified from the lysate. More preferred is wherein the lysate is incubated before the purification step.

In another aspect, the invention provides a method of preventing N-terminal cleavage of an amino acid residue from a polypeptide comprising culturing the cells described above, wherein the cells comprise a nucleic acid encoding the polypeptide, under conditions such that the nucleic acid is expressed. Preferably, the polypeptide is recovered from the cells. In addition, preferably the polypeptide is heterologous to the cells, more preferably eukaryotic, more preferably mammalian, and most preferably human. The cell is preferably an *E. coli* cell.

In a further aspect, the invention provides a method for cleaving an N-terminal amino acid from a polypeptide isolated from a cell comprising contacting the polypeptide with an aminopeptidase encoded by a nucleic acid that has at least an 80% sequence identity to (a) a DNA molecule encoding a native-sequence aminopeptidase b2324 having the sequence of amino acid residues from 1 to 688 of SEQ ID NO:2, or (b) the complement of the DNA molecule of (a). Preferably, the polypeptide is incubated with the aminopeptidase.

Alternatively, a method is provided for cleaving an N-terminal amino acid from a polypeptide isolated from a cell comprising contacting the polypeptide with an aminopeptidase that has at least an 80% sequence identity to native-sequence aminopeptidase b2324 having the sequence of amino acid residues from 1 to 688 of SEQ ID NO:2.

In a specific aspect, a method is provided for cleaving an N-terminal amino acid from a polypeptide comprising contacting the polypeptide with native-sequence aminopeptidase b2324.

In another embodiment, a method of producing a cleaved polypeptide is comprising culturing gram-negative bacterial cells harboring a nucleic acid having at least an 80% sequence identity to (a) a DNA molecule encoding a native-sequence aminopeptidase b2324 having the sequence of amino acid residues from 1 to 688 of SEQ ID NO:2, or (b) the complement of the DNA molecule of (a) and encoding an aminopeptidase, which cells comprise nucleic acid encoding the corresponding uncleaved polypeptide that has an added amino acid at its N-terminus, wherein the culturing is under conditions so as to express or overexpress the gene and so as to express the nucleic acid encoding the uncleaved polypeptide, and if the uncleaved polypeptide and aminopeptidase are not in contact after expression, contacting the uncleaved polypeptide with the aminopeptidase so as to produce the cleaved polypeptide. In a preferred aspect, the polypeptide is heterologous to the cells, more preferably eukaryotic, even more preferably mammalian, and most preferably human.

In another aspect, the invention provides a method of producing a cleaved polypeptide comprising culturing gram-negative bacterial cells harboring a nucleic acid having at least an 80% sequence identity to native-sequence yfcK gene having the sequence of nucleotides from 1 to 2067 of SEQ ID NO:1 and encoding an aminopeptidase, which cells comprise nucleic acid encoding the corresponding uncleaved polypeptide that has an added amino acid at its N-terminus, wherein the culturing is under conditions so as to express or overexpress the gene and so as to express the nucleic acid encoding the uncleaved polypeptide, and if the uncleaved polypeptide and aminopeptidase are not in contact after expression, contacting the uncleaved polypeptide with the aminopeptidase so as to produce the cleaved polypeptide.

In another aspect, the invention provides a method of producing a cleaved polypeptide comprising culturing *E. coli* cells harboring native-sequence yfcK gene and comprising nucleic acid encoding the corresponding uncleaved polypeptide that has an added amino acid at its N-terminus, wherein the culturing is under conditions so as to express or overexpress the yfcK gene and to express the nucleic acid encoding the uncleaved polypeptide, and if the uncleaved polypeptide and native-sequence aminopeptidase b2324 encoded by the yfcK gene are not in contact after expression, contacting the uncleaved polypeptide with native-sequence aminopeptidase b2324 so as to produce the cleaved polypeptide.

In the above methods for producing a cleaved polypeptide, preferred aspects include those wherein the cell is deficient in at least one gene encoding a protease, and/or the culturing conditions are such that the yfcK gene (native-sequence and homologs) is overexpressed, and/or the contacting is by incubation. The yfcK gene (native-sequence and homologs) may be native to the bacterial cells or introduced to the bacterial cells. The culturing preferably takes place in a fermentor. The uncleaved polypeptide is preferably recovered from the cells before contact with the aminopeptidase, wherein the recovery may be from the periplasm or culture medium of the cells or by cell disruption to form a lysate from which preferably the cleaved polypeptide is purified. Also the lysate may be incubated before the purification step. Preferably the lysate is incubated for at least about 1 hour, more preferably about 2-50 hours, at about 20-40° C., more preferably at about 30-40° C.

BRIEF DESCRIPTION OF THE DRAWINGS

FIG. 1 depicts a diagram of the derivation of *E. coli* cell 61G3, a host strain deleted for yfcK (encoding b2324).

FIG. 2 shows a bar graph of percent area (liquid chromatography/mass spectroscopy; LC/MS) of the rhGH extraction control strain 16C9 incubated at room temperature for 0, 15, 24, and 42 hours, with the native hGH, des-phenylalanine hGH, and des-phenylalanine-proline hGH amounts shown in different shades.

FIG. 3 shows a bar graph of percent area (LC/MS) of the rhGH strain 61G3 that has the deleted gene incubated at room temperature for 0, 15, 24, and 42 hours, with the native hGH, des-phenylalanine hGH, and des-phenylalanine-proline hGH amounts shown in different shades.

FIG. 4 shows a bar graph of percent area (liquid chromatography/mass spectroscopy; LC/MS) of the rhGH extraction control strain 16C9 incubated at 37° C. for 0, 15, and 24 hours, with the native hGH, des-phenylalanine hGH, and des-phenylalanine-proline hGH amounts shown in different shades.

FIG. 5 shows a bar graph of percent area (LC/MS) of the rhGH strain 61G3 that has the deleted gene incubated at 37° C. for 0, 15, and 24 hours, with the native hGH, des-phenylalanine hGH, and des-phenylalanine-proline hGH amounts shown in different shades.

DETAILED DESCRIPTION OF THE PREFERRED EMBODIMENTS

Definitions

As used herein, the expressions "cell," "cell line," "strain," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The "bacteria" for purposes herein are gram-negative bacteria. One preferred type of bacteria is *Enterobacteriaceae*. Examples of bacteria belonging to *Enterobacteriaceae* include *Escherichia, Enterobacter, Erwinia, Klebsiella, Proteus, Salmonella, Serratia,* and *Shigella*. Other types of suitable bacteria include *Azotobacter, Pseudomonas, Rhizobia, Vitreoscilla,* and *Paracoccus*. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting, and W3110 is preferred. Mutant cells of any of the above-mentioned bacteria may also be employed. It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

The "chromosomal yfcK gene" refers to the gene encoding a protein b2324 listed as a "putative peptidase" by the *E. coli* genome sequencing project (Blattner et al., supra) in the GenBank database (accession number AE000321). The protein has Dayhoff accession number B65005 and SwissProt accession number P77182, and the gene is located on the *E. coli* chromosome at 52.59', and its base pair location=Left End: 2439784 bp Right End: 2441790 bp. Its gene sequence is:

```
                                                   (SEQ ID NO:1)
TTGCGCAGCCTTACACACATCGCTAAGATCGAGCCACCGCCTGTAAGACG
AGTAACTTACGTGAAACACTACTCCATACAACCTGCCAACCTCGAATTTA
ATGCTGAGGGTACACCTGTTTCCCGAGATTTTGACGATGTCTATTTTTCC
AACGATAACGGGCTGGAAGAGACGCGTTATGTTTTCTGGGAGGCAACCA
ATTAGAGGTACGCTTTCCTGAGCATCCACATCCTCTGTTTGTGGTAGCAG
AGAGCGGCTTCGGCACCGGATTAAACTTCCTGACGCTATGGCAGGCATTT
GATCAGTTTCGCGAAGCGCATCCGCAAGCGCAATTACAACGCTTACATTT
CATTAGTTTTGAGAAATTTCCCCTCACCCGTGCGGATTTAGCCTTAGCGC
ATCAACACTGGCCGGAACTGGCTCCGTGGGCAGAACAACTTCAGGCGCAG
TGGCCAATGCCCTTGCCCGGTTGCCATCGTTTATTGCTCGATGAAGGCCG
CGTGACGCTGGATTTATGGTTTGGCGATATTAACGAACTGACCAGCCAAC
TGGACGATTCGCTAAATCAAAAAGTAGATGCCTGGTTTCTGGACGGCTTT
GCGCCAGCGAAAAACCCGGATATGTGGACGCAAAATCTGTTTAACGCCAT
GGCAAGGTTGGCGCGTCCGGGCGGCACGCTGGCGACATTTACGTCTGCCG
GTTTTGTCCGCCGCGGTTTGCAGGACGCCGGATTCACGATGCAAAAACGT
AAGGGCTTTGGGCGCAAACGGGAAATGCTTTGCGGGGTGATGGAACAGAC
ATTACCGCTCCCCTGCTCCGCGCCGTGGTTTAACCGCACGGGCAGCAGCA
AACGGGAAGCGGCGATTATCGGCGGTGGTATTGCCAGCGCGTTGTTGTCG
CTGGCGCTATTACGGCGCGGCTGGCAGGTAACGCTTTATTGCGCGGATGA
GGCCCCCGCACTGGGTGCTTCCGGCAATCGCCAGGGGGCGCTGTATCCGT
TATTAAGCAAACACGATGAGGCGCTAAACCGCTTTTTCTCTAATGCGTTT
ACTTTTGCTCGTCGGTTTTACGACCAATTACCCGTTAAATTTGATCATGA
CTGGTGCGGCGTCACGCAGTTAGGCTGGGATGAGAAAAGCCAGCATAAAA
TCGCACAGATGTTGTCAATGGATTTACCCGCAGAACTGGCTGTAGCCGTT
GAGGCAAATGCGGTTGAACAAATTACGGGCGTTGCGACAAATTGCAGCGG
CATTACTTATCCGCAAGGTGGTTGGCTGTGCCCAGCAGAACTGACCCGTA
ATGTGCTGGAACTGGCGCAACAGCAGGGTTTGCAGATTTATTATCAATAT
CAGTTACAGAATTTATCCCGTAAGGATGACTGTTGGTTGTTGAATTTTGC
AGGAGATCAGCAAGCAACACACAGCGTAGTGGTACTGGCGAACGGGCATC
AAATCAGCCGATTCAGCCAAACGTCGACTCTCCCGGTGTATTCGGTTGCC
GGGCAGGTCAGCCATATTCCGACAACGCCGGAATTGGCAGAGCTGAAGCA
GGTGCTGTGCTATGACGGTTATCTCACGCCACAAAATCCGGCGAATCAAC
ATCATTGTATTGGTGCCAGTTATCATCGCGGCAGCGAAGATACGGCGTAC
AGTGAGGACGATCAGCAGCAGAATCGCCAGCGGTTGATTGATTGTTTCCC
GCAGGCACAGTGGGCAAAAGAGGTTGATGTCAGTGATAAAGAGGCGCGCT
GCGGTGTGCGTTGTGCCACCCGCGATCATCTGCCAATGGTAGGCAATGTT
CCCGATTATGAGGCAACACTCGTGGAATATGCGTCGTTGGCGGAGCAGAA
AGATGAGGCGGTAAGCGCGCCGGTTTTTGACGATCTCTTTATGTTTGCGG
CTTTAGGTTCTCGCGGTTTGTGTTCTGCCCCGCTGTGTGCCGAGATTCTG
GCGGCGCAGATGAGCGACGAACCGATTCCGATGGATGCCAGTACGCTGGC
GGCGTTAAACCCGAATCGGTTATGGGTGCGGAAATTGTTGAAGGGTAAAG
CGGTTAAGGCGGGGTAA;
``` and the protein encoded by it has the sequence:

```
                                                   (SEQ ID NO:2)
MRSLTHIAKIEPPPVRRVTYVKHYSIQPANLEFNAEGTPVSRDFDDVYFS
NDNGLEETRYVFLGGNQLEVRFPEHPHPLFVVAESGFGTGLNFLTLWQAF
DQFREAHPQAQLQRLHFISFEKFPLTRADLALAHQHWPELAPQAEQLQAQ
WPMPLPGCHRLLLDEGRVTLDLWFGDINELTSQLDDSLNQKVDAWFLDGF
APAKNPDMWTQNLFNAMARLARPGGTLATFTSAGFVRRGLQDAGFTMQKR
KGFGRKREMLCGVMEQTLPLPCSAPWFNRTGSSKREAAIIGGGIASALLS
LALLRRGWQVTLYCADEAPALGASGNRQGALYPLLSKHDEALNRFFSNAF
TFARRFYDQLPVKFDHDWCGVTQLGWDEKSQHKIAQMLSMDLPAELAVAV
EANAVEQITGVATNCSGITYPQGGWLCPAELTRNVLELAQQQGLQIYYQY
QLQNLSRKDDCWLLNFAGDQQATHSVVVLANGHQISRFSQTSTLPVYSVA
GQVSHIPTTPELAELKQVLCYDGYLTPQNPANQHHCIGASYHRGSEDTAY
SEDDQQQNRQRLIDCFPQAQWAKEVDVSDKEARCGVRCATRDHLPMVGNV
PDYEATLVEYASLAEQKDEAVSAPVFDDLFMFAALGSRGLCSAPLCAEIL
AAQMSDEPIPMDASTLAALNPNRLWVRKLLKGKAVKAG.
```

"Deficient" in a gene or nucleic acid means that the cell has the gene in question deleted or inactivated or disabled so that it does not produce the protein that it encodes. For example, cells deficient in the chromosomal yfcK gene encoding b2324 do not produce the product of that gene when cultured. Similarly, a cell deficient in a gene encoding a protease does not produce that particular protease when cultured.

As used herein, "polypeptide" refers generally to peptides and proteins from any cell source having more than about ten amino acids. "Heterologous" polypeptides are those polypeptides foreign to the host cell being utilized, such as a human protein produced by *E. coli*. While the heterologous polypeptide may be prokaryotic or eukaryotic, preferably it is eukaryotic, more preferably mammalian, most preferably human.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C;

atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides. One preferred set of polypeptides of interest are those having an N-terminal phenylalanine, such as hGH. Another preferred set of polypeptides of interest is those produced in the periplasm or cell culture medium of the bacteria, such as hGH.

The expression "control sequences" refers to DNA sequences necessary for the expression of an operably linked coding sequence in a particular host organism. The control sequences that are suitable for bacteria include a promoter, optionally an operator sequence, and a ribosome binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. Linking is accomplished, for example, by ligation at convenient restriction sites. If such sites do not exist, the synthetic oligonucleotide adaptors or linkers are used in accordance with conventional practice.

The term "overexpression" with respect to a gene or nucleic acid refers to synthesis of specific proteins in larger quantities than is usually produced by the cell when there is no artificial induction of such synthesis, as, e.g., by means of a promoter.

The term "recovery" of a polypeptide generally means obtaining the polypeptide free from the cells in which it was produced.

The terms "aminopeptidase b2324 polypeptide", "aminopeptidase b2324 protein" and "aminopeptidase b2324" when used herein encompass native-sequence aminopeptidase b2324 and aminopeptidase b2324 homologs (which are further defined herein). Depending on the context, the aminopeptidase b2324 polypeptides may be isolated from a variety of sources, such as from the bacterial cells, or prepared by recombinant and/or synthetic methods.

A "native-sequence aminopeptidase b2324" comprises a polypeptide having the same amino acid sequence as an aminopeptidase b2324 derived from nature. Such native-sequence aminopeptidase b2324 can be isolated from nature or can be produced by recombinant and/or synthetic means. The term "native-sequence aminopeptidase b2324" specifically encompasses naturally occurring truncated or secreted forms (e.g., an extracellular domain sequence), naturally occurring variant forms (e.g., alternatively spliced forms) and naturally occurring allelic variants of the aminopeptidase b2324. In one embodiment of the invention, the native-sequence aminopeptidase b2324 is a mature or full-length native sequence aminopeptidase b2324 comprising amino acids 1 to 688 of SEQ ID NO:2.

"Aminopeptidase b2324 homolog" means an aminopeptidase having at least about 80% amino acid sequence identity with the amino acid sequence of residues 1 to 688 of the aminopeptidase b2324 polypeptide having the amino acid sequence of SEQ ID NO:2. Such aminopeptidase b2324 homologs include, for instance, aminopeptidase b2324 polypeptides wherein one or more amino acid residues are added, or deleted, at the N- or C-terminus, as well as within one or more internal domains, of the sequence of SEQ ID NO:2. Preferably, an aminopeptidase 2324 homolog will have at least about 85% amino acid sequence identity, more preferably at least about 90% amino acid sequence identity, and even more preferably at least about 95% amino acid sequence identity with the amino acid sequence of residues 1 to 688 of SEQ ID NO:2. Homologs do not encompass the native sequence.

A yfcK gene indicates a gene having at least an 80% sequence identity to (a) a DNA molecule encoding a native-sequence aminopeptidase b2324 having the sequence of amino acid residues from 1 to 688 of SEQ ID NO:2, or (b) the complement of the DNA molecule of (a), and encoding an aminopeptidase, and also indicates a gene having at least an 80% sequence identity to a chromosomal yfcK gene having the complete sequence of nucleic acid residues of SEQ ID NO:1 and encoding an aminopeptidase. Such yfcK genes include, for instance, the chromosomal yfcK gene wherein one or more nucleic acid residues are added, or deleted, at the 5'- or 3'-end, as well as within an internal portion, of the sequence of SEQ ID NO:1. Preferably, a yfcK gene will have at least about 85% nucleic acid sequence identity, more preferably at least about 90% nucleic acid sequence identity, and even more preferably at least about 95% nucleic acid sequence identity, with the nucleic acid sequence of nucleotides 1 to 2067 of SEQ ID NO:1. This term includes the native-sequence yfcK gene (i.e., the chromosomal yfcK gene).

"Percent (%) amino acid sequence identity" with respect to the aminopeptidase b2324 sequences identified herein is defined as the percentage of amino acid residues in a candidate sequence that are identical with the amino acid residues in the aminopeptidase b2324 sequence, after aligning the sequences and introducing gaps, if necessary, to achieve the maximum percent sequence identity, and not considering any conservative substitutions as part of the sequence identity. The % identity values used herein may be generated by WU-BLAST-2 which was obtained from (Altschul et al., *Methods in Enzymology*, 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" with respect to the coding sequence of the aminopeptidase b2324 polypeptides identified herein is defined as the percentage of nucleotide residues in a candidate sequence that are identical with the nucleotide residues in the aminopeptidase b2324 coding sequence. The identity values used herein may be generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the aminopeptidase b2324 natural environment will not be present. Ordinarily, however, isolated polypeptide will be prepared by at least one purification step.

An "isolated" nucleic acid molecule encoding an aminopeptidase b2324 polypeptide is a nucleic acid molecule that is identified and separated from at least one contaminant nucleic acid molecule with which it is ordinarily associated in the natural source of the aminopeptidase b2324-encoding nucleic acid. An isolated aminopeptidase b2324-encoding nucleic acid molecule is other than in the form or setting in which it is found in nature. Isolated nucleic acid molecules therefore are distinguished from the aminopeptidase b2324-encoding nucleic acid molecule as it exists in natural cells. However, an isolated nucleic acid molecule encoding an aminopeptidase b2324 polypeptide includes aminopeptidase b2324-encoding nucleic acid molecules contained in cells that ordinarily express aminopeptidase b2324 where, for example, the nucleic acid molecule is in a chromosomal location different from that of natural cells.

Modes for Carrying Out the Invention

In one aspect, the invention relates to certain bacterial host cell strains that lack an aminopeptidase (i.e., an enzyme that clips off the amino acid residue located at the N-terminus of polypeptides, such as one that clips between an N-terminal phenylalanine and another amino acid adjacent to it), thereby allowing improved purification of the polypeptide.

Specifically, the present invention provides, in this aspect, gram-negative bacterial cells deficient in a chromosomal gene (which gene is not deficient in a wild-type version of such cells) having at least an 80% sequence identity to (a) a DNA molecule encoding a native-sequence aminopeptidase b2324 having the sequence of amino acid residues from 1 to 688 of SEQ ID NO:2, or (b) the complement of the DNA molecule of (a), and encoding an aminopeptidase. That is, such a gene shares at least an 80% sequence identity to the sequence of the yfcK gene. Preferably, this gene shares at least about 85% sequence identity, more preferably at least about 90% sequence identity, still more preferably at least about 95% sequence identity, and most preferably 100% sequence identity with the sequence of the yfcK gene (which encodes the native-sequence aminopeptidase b2324).

In another aspect, the gram-negative bacterial cells are deficient in a chromosomal gene (which gene is not deficient in a wild-type version of such cells) encoding an aminopeptidase that has at least an 80% sequence identity to native-sequence aminopeptidase b2324 having the sequence of amino acid residues from 1 to 688 of SEQ ID NO:2. Preferably, the aminopeptidase has at least an about 85%, more preferably at least an about 90%, more preferably still at least an about 95% sequence identity. This includes cells deficient in chromosomal native-sequence yfcK gene.

In a third aspect, the gram-negative bacterial cells are deficient in a chromosomal gene (which gene is not deficient in a wild-type version of such cells) which gene comprises (a) DNA encoding a polypeptide scoring at least 80% positives when compared to the sequence of amino acid residues of native-sequence aminopeptidase b2324 spanning from 1 to 688 of SEQ ID NO:2, or (b) the complement of the DNA of (a), said polypeptide being an aminopeptidase. This includes cells having 100% positives when compared to the native sequence of aminopeptidase b2324.

The cells that are the subject of this aspect of the invention are gram-negative bacteria, for example, the bacteria with sequenced genomes such as *Salmonella, Yersinia, Haemophilus, Caulobacter, Agrobacterium, Vibrio* etc.), where a yfcK homolog is predicted. More preferably, the cell is *Salmonella* or *Enterobacteriaceae*, still more preferably *E. coli*, most preferably W3110.

The cell is optionally further deficient in one or more other chromosomal genes present in the wild-type versions of such cells, such as those genes encoding bacterial proteases. *E. coli* strains deficient in proteases or genes controlling the regulation of proteases are known (Beckwith and Strauch, WO 88/05821 published Aug. 11, 1988; Chaudhury and Smith, *J. Bacteriol.*, 160: 788-791 (1984); Elish et al., *J. Gen. Microbiol.*, 134: 1355-1364 (1988); Baneyx and Georgiou, "Expression of proteolytically sensitive polypeptides in *Escherichia coli*," In: *Stability of Protein Pharmaceuticals*, Vol. 3: Chemical and Physical Pathways of Protein Degradation, Ahern and Manning, eds. (Plenum Press, New York, 1992), p. 69-108).

Some of these protease-deficient strains have been used in attempts to efficiently produce proteolytically sensitive peptides, particularly those of potential medical or commercial interests. U.S. Pat. No. 5,508,192 (to Georgiou et al) describes the construction of many protease-deficient and/or heat-shock protein-deficient bacterial hosts. Such hosts include single, double, triple, or quadruple protease-deficient bacteria and single-protease bacteria that also carry a mutation in the rpoH gene. Examples of the protease genes disclosed include degP ompT ptr3, prc (tsp), and a degP rpoH strain reported to produce large titers of recombinant proteins in E. coli. Park et al., Biotechnol. Prog., 15: 164-167 (1999) also reported that a strain (HM114) deficient in two cell envelope proteases (degP prc) grew slightly faster and produced more fusion protein than the other strains deficient in more proteases. The cells herein may be deficient in any one or more of such proteases, with preferred such proteases being chromosomal ptr3 encoding Protease III, chromosomal ompT encoding protease OmpT, and/or chromosomal degP encoding protease DegP. The strains may also be deficient in tonA (fhuA), phoA, and/or deoC. Preferably the cell is deficient in degP and/or fhuA. Most preferably, the cell has the genotype W3110 ΔfhuA Δ(arg-F-lac)169 phoAΔE15 deoC2 degP::kanR ilvG2096 ΔyfcK.

In another embodiment, the cell comprises a nucleic acid encoding a polypeptide heterologous to the cell. The nucleic acid may be introduced into the cell by any means, but is preferably used to transform the nucleic acid, as by use of a recombinant expression vector or by homologous recombination, most preferably by a vector.

Examples of suitable heterologous polypeptides are those defined above and include proteins and polypeptides that start with a methionine residue and have phenylalanine as the second residue, as well as proteins that start with a phenylalanine (i.e., those that in the mature form start with a phenylalanine or are further processed proteolytically to remove the initial methionine and those that are preproproteins that have the signal peptide cleaved to leave the Phe as the N-terminus of the mature protein such as human growth hormone). Hence, any polypeptide heterologous to the bacterial cell in which it is made where the amino terminus of the mature or final product is Phe is included herein for this purpose.

Examples of human polypeptides meeting this requirement of the phenylalanine placement include collagen alpha 2 chain precursor, T-cell surface glycoprotein cd3 delta chain precursor, insulin precursor, integrin alpha-3 precursor, integrin alpha-5 precursor, integrin alpha-6 precursor, integrin alpha-7 precursor, integrin alpha-e precursor, integrin alpha-m precursor, integrin alpha-v precursor, integrin alpha-x precursor, phosphatidylcholine-sterol acyltransferase precursor, lymphocyte function-associated antigen 3 precursor, interstitial collagenase precursor, neutrophil collagenase precursor, motilin precursor, neuropilin-1 precursor, platelet-activating factor acetylhydrolase precursor, bone sialoprotein ii precursor, growth hormone variant precursor (Seeburg, DNA 1: 239-249 (1982)), somatotropin precursor, small inducible cytokine a13 precursor, small inducible cytokine a27 precursor, small inducible cytokine b11 precursor, tumor necrosis factor receptor superfamily member 8 precursor, thyrotropin beta chain precursor, vascular endothelial growth factor c precursor, preproinsulin (BE885196-A), human growth hormone variant HGH-V (EP89666-A), human proinsulin (U.S. Pat. No. 4,431,740), AP signal peptide and human growth hormone (hGH) encoded by pAP-1 (EP177343-A), human growth hormone (hGF) precursor (EP245138-A), human BMP (EP409472-A) human LFA-3 (CD58) protein (DE4008354-A), human type II interleukin-1 receptor (EP460846-A), aprotinin analogue #6 with reduced nephrotoxicity (WO9206111-A), aprotinin analogue #7 with reduced nephrotoxicity (WO9206111-A), aprotinin analogue #8 with reduced nephrotoxicity (WO9206111-A), aprotinin analogue #10 with reduced nephrotoxicity (WO9206111-A), aprotinin analogue #9 with reduced nephrotoxicity (WO9206111-A), aprotinin analogue #11 with reduced nephrotoxicity (WO9206111-A), aprotinin analogue #12 with reduced nephrotoxicity (WO9206111-A), aprotinin analogue #13 with reduced nephrotoxicity (WO9206111-A), aprotinin analogue #14 with reduced nephrotoxicity (WO9206111-A), alpha 6A integrin subunit (WO9219647-A), alpha 6B integrin subunit (WO9219647-A), human LFA-3 protein (EP517174-A), human plasma carboxypeptidase B (U.S. Pat. No. 5,206,161-A), lymphoblastoid derived IL-1R (WO9319777-A), human LFA-3 (JP06157334-A), human receptor induced by lymphocyte activation (ILA) (CA2108401-A), endothelial cell protein receptor (WO9605303-A1), human lecithin-cholesterol acyltransferase (LCAT) (WO9717434-A2), human soluble CD30 antigen (DE9219038-U1), human small CCN-like growth factor (WO9639486-A1), human plasma carboxypeptidase B (U.S. Pat. No. 5,593,674-A), human growth hormone (WO9820035-A1), insulin analogue encoded by a plasmid pKFN-864 fragment (EP861851-A1), primate CXC chemokine "IBICK" polypeptide (WO9832858-A2), human small CCN-like growth factor (U.S. Pat. No. 5,780,263-A), amino acid sequence of human plasma hyaluronidase (hpHAse) (WO9816655-A1), human Type II IL-1R protein (U.S. Pat. No. 5,767,064-A), homo sapiens clone CC365_40 protein (WO9807859-A2), human growth hormone (U.S. Pat. No. 5,955,346-A), human soluble growth hormone receptor (U.S. Pat. No. 5,955,346-A), human CD30 antigen protein (WO9940187-A1), human neuropilin-1 (WO9929858-A1), human brain tissue-derived polypeptide (clone OMB096) (WO9933873-A1), human Toll protein PRO285 (WO9920756-A2), amino acid sequence of a human secreted peptide (WO9911293-A1), amino acid sequence of a human secreted peptide (WO9911293-A1), amino acid sequence of a human secreted peptide (WO9911293-A1), amino acid sequence of a human secreted peptide (WO9911293-A1), amino acid sequence of a human secreted protein (WO9907891-A1), amino acid sequence of a human secreted protein (WO9907891-A1), amino acid sequence of a human secreted protein (WO9907891-A1), human plasma carboxypeptidase B (PCPB) thr147 (WO9855645-A1), human chemokine MIG-beta protein (EP887409-A1), amino acid sequence of a human secretory protein (WO200052151-A2), human hGH/EGF fusion protein encoded by plasmid pWRG1630 (U.S. Pat. No. 6,090,790-A), human secreted protein encoded by cDNA clone 3470865 (WO200037634-A2), human monocyte-derived protein FDF03Delta™ (WO200040721-A1), human monocyte-derived protein FDF03-S1 (WO200040721-A1), human monocyte-derived protein FDF03-M14 (WO200040721-A1), human monocyte-derived protein FDF03-S2 (WO200040721-A1), human secreted protein #2 (EP1033401-A2), human prepro-vascular endothelial growth factor C (WO200021560-A1), human membrane transport protein, MTRP-15 (WO200026245-A2), human vascular endothelial growth factor (VEGF)-C protein (WO200024412-A2), human TANGO 191 (WO200018800-A1), interferon Receptor-HKAEF92 (WO9962934-A1), human integrin subunit alpha-10 (WO9951639-A1), human integrin subunit alpha-10 splice variant (WO9951639-A1), human delta 1-pyrroline-5-carboxylate reductase homologue (P5CRH) (U.S. Pat. No. 6,268,192-B1), human growth/differentiation factor-6-like protein AMF10 (WO200174897-A2), human transporter and ion channel-6 (TRICH-6) protein (WO200162923-A2), human transporter and ion channel-7 (TRICH-7) protein (WO200162923-A2), human matrix metalloprotinase-1 (MMP-1) protein (WO200166766-A2), human matrix metalloprotinase-8 (MMP-8) protein (WO200166766-A2), human matrix metalloprotinase-18P (MMP-18P) protein (WO200166766-A2), human G-protein coupled receptor 6 (GPCR6) protein (WO200181378-A2), human Zlec1 protein (WO200166749-A2), human matrix metalloprotease (MMP)-like protein (WO200157255-A1), human gene 15 encoded secreted protein HFXDI56 (WO200154708-A1), human gene 9 encoded secreted protein HTEGF16, (WO200154708-A1), human secreted protein (SECP) #4 (WO200151636-A2), human gene 20 encoded secreted protein HUSIB13 (WO200151504-A1), human gene 28 encoded secreted protein HISAQ04 (WO200151504-A1), human gene 35 encoded secreted protein HCNAH57 (WO200151504-A1), human gene 17 encoded secreted protein HBMCF37 (WO200151504-A1), human tumour necrosis factor (TNF) stimulated gene-6 (TSG-6) protein (U.S. Pat. No. 6,210,905-B1), FCTR10 (WO200146231-A2), human gene 18 encoded secreted protein HFKHW50 (WO200136440-A1), human gene 18 encoded secreted protein HFKHW50 (WO200136440-A1), human gene 13 encoded secreted protein HE8FC45 (WO200077022-A1), human gene 32 pk encoded secreted protein HTLIF12 (WO200077022-A1), human gene 4 encoded secreted protein HCRPV17 (WO200134643-A1), human gene 23 encoded secreted protein HE8O K73 (WO200134643-A1), human gene 4 encoded secreted protein HCRPV17 (WO200134643-A1), human gene 22 encoded secreted protein HMSFK67 (WO200132676-A1), human gene 22 encoded secreted protein HMSFK67 (WO200132676-A1), human gene 22 encoded secreted protein HMSFK67 (WO200132676-A1), human gene 19 encoded secreted protein HCRNF14 (WO200134800-A1), human gene 6 encoded secreted protein HNEEB45 (WO200132687-A1), human gene 6 encoded secreted protein HNEEB45 (WO200132687-A1), human gene 9 encoded secreted protein HHPDV90 (WO200132675-A1), human gene 1 encoded secreted protein B7-H6 (WO200134768-A2), human gene 3 encoded secreted protein HDPMS12 (WO200134768-A2), human gene 13 encoded secreted protein clone HRABS65 (WO200134768-A2), human gene 1 encoded secreted protein HDPAP35 (WO200134768-A2), human gene 3 encoded secreted protein HDPMS12 (WO200134768-A2), human gene 17 encoded secreted protein HACCL63 (WO200134769-A2), human gene 17 encoded secreted protein HACCL63 (WO200134769-A2), human gene 10 encoded secreted protein HHEPJ23 (WO200134629-A1), human gene 10 encoded secreted protein HHEPJ23 (WO200134629-A1), human gene 5 encoded secreted protein HE9QN39 (WO200134626-A1), human gene 14 encoded secreted protein HCRNO87 (SEQ 104) (WO200134626-A1), human gene 5 encoded secreted protein HE9QN39 (WO200134626-A1), human gene 14 encoded secreted protein HCRNO87 (SEQ 145) (WO200134626-A1), human gene 4 encoded secreted protein HSODE04 (WO200134623-A1), human gene 6 encoded secreted protein HMZMF54 (WO200134623-A1), human gene 18 encoded secreted protein HPJAP43 (WO200134623-A1), human gene 27 encoded secreted protein HNTSL47 (WO200134623-A1), human gene 4 encoded secreted protein HSODE04 (WO200134623-A1), human gene 6 encoded secreted protein HMZMF54 (WO200134623-A1), human gene 18 encoded secreted protein HPJAP43 (WO200134623-A1), human gene 27 encoded secreted protein HNTSL47 (WO200134623-A1), human gene 21 encoded secreted protein HLJEA01 (WO200134767-A2), human gene 25 encoded secreted protein HTJNX29 (SEQ 115) (WO200134627-A1), human gene 25 encoded secreted protein HTJNX29 (SEQ 165) (WO200134627-A1), human TANGO 509 amino acid sequence (WO200121631-A2), human TANGO 210 protein (WO200118016-A1), human cancer related protein 12 (WO200118014-A1), human cancer related protein 18 (WO200118014-A1), human B7-4 secreted (B7-4S) protein (WO200114557-A1), human B7-4 membrane (B7-4M) protein (WO200114557-A1), human B7-4 secreted (B7-4S) protein (WO200114556-A1), human B7-4 membrane (B7-4M) protein (WO200114556-A1), human interleukin DNAX 80 variant (WO200109176-A2), human lecithin-cholesterol acyltransferase (LCAT) (WO200105943-A2), amino acid sequence of human polypeptide PRO1419 (WO200077037-A2), amino acid sequence of a human alpha11 integrin chain (WO200075187-A1), human A259 (WO200073339-A1), human bone marrow derived peptide (WO200166558-A1), human tumour-associated antigenic target-169 (TAT169) protein (WO200216602-A2), human gene 3 encoded secreted protein HKZAO35ID (WO200218411-A1), human gene 3 encoded secreted protein HKZAO35 (WO200218411-A1), human gene 11 encoded secreted protein HLYCK27 (WO200218435-A1), human INTG-1 protein (WO200212339-A2), human gene 15 encoded secreted protein HFPHA80, SEQ 70 (WO200216390-A1), human gene 15 encoded secreted protein HFPHA80, SEQ 94 (WO200216390-A1), human gene 2 encoded secreted protein HDQFU73, SEQ 69 (WO200224719-A1), human gene 8 encoded secreted protein HDPTC31, SEQ 75 (WO200224719-A1), human gene 2 encoded secreted protein HDQFU73, SEQ 90 (WO200224719-A1), human gene 6 encoded secreted protein HDPRJ60, SEQ 95 (WO200224719-A1), human gene 8 encoded secreted protein HDPTC31, SEQ 99 (WO200224719-A1), human gene 8 encoded secreted protein HDPTC31, SEQ 100 (WO200224719-A1), human proinsulin analog (WO200204481-A2), tumour-associated antigenic target protein, TAT136 (WO200216429-A2), tumour associated antigenic target polypeptide (TAT) 136 (WO200216581-A2), human CD30 protein sequence (WO200211767-A2), human interleukin 1R2 (IL-1R2) protein sequence (WO200211767-A2), human G-protein coupled receptor-7 (GPCR-7) protein (WO200206342-A2), human G-protein coupled-receptor (GPCR6a) (WO200208289-A2), human G-protein coupled-receptor (GPCR6b) (WO200208289-A2), human type II Interleukin-1 receptor (WO200187328-A2), human A259 polypeptide (WO200181414-A2), human vascular cell adhesion molecule, VCAM1 (U.S. Pat. No. 6,307,025-B1), human vascular cell adhesion molecule, VCAM1b (U.S. Pat. No. 6,307,025-B1), human transporters and ion channels (TRICH)-6 (WO200177174-A2), and human protein modification and maintenance molecule-8 (PMMM-8) (WO200202603-A2).

In a further aspect, the invention provides a method for producing a heterologous polypeptide comprising (a) culturing the cell harboring the nucleic acid encoding the heterologous polypeptide and (b) recovering the polypeptide from the cell. The recovery may be from the cytoplasm, periplasm, or culture medium of the cell, although preferably the polypeptide is recovered from the periplasm or culture medium of the cell. Preferably the culturing takes place in a fermentor. Culturing parameters are used and polypeptide production is conducted in a conventional manner, such as those procedures described below.

When the desired polypeptide is produced in the cytoplasm, incubation upon pre- or post-lysis of the cells is not necessary, although it may increase the efficiency of the formation of clipped material. When the desired polypeptide is secreted into the periplasm or cell culture medium, then an incubation step is preferred and recommended for at least about 0.5 hour. The preferred method for recovering periplasmically produced polypeptides is to disrupt or break the cells, using, for example, homogenizers, French pressure cells, and microfluidizers for larger volumes and sonicators for smaller volumes. A lysate is formed from the disrupted cells from which intact polypeptide can be purified. Preferably such lysate is incubated before the purification step. This incubation can be conducted at any suitable temperature, but preferably is at room temperature or less for at least about 1 hour, more preferably for about 2-50 hours. The polypeptide and cell type are preferably as set forth above.

Additionally, the invention provides a method of preventing N-terminal cleavage of an amino acid residue from a polypeptide comprising culturing the cell, wherein the cell comprises a nucleic acid encoding the polypeptide, under conditions such that the nucleic acid is expressed. Such culturing conditions are conventional and well known to those skilled in the art. Preferably, the polypeptide is recovered from the cell. The preferred polypeptide and cell type are described above.

Alternatively, the reverse situation applies where the cleaved polypeptide is being purified from the uncleaved polypeptide that is the impurity. In this aspect, the invention provides a method for cleaving an N-terminal amino acid from a polypeptide comprising contacting the polypeptide with the aminopeptidase b2324 protein as described above, preferably wherein the contacting is by incubation with the aminopeptidase b2324 protein. A further method for producing a cleaved polypeptide involves culturing bacteria cells harboring a yfcK gene (whether the gene is endogenous or heterologous to the cells) and comprising nucleic acid encoding the corresponding uncleaved polypeptide that has an added amino acid at its N-terminus, wherein the culturing is under conditions so as to express or overexpress the yfcK gene and to express the nucleic acid encoding the uncleaved polypeptide, and if the uncleaved polypeptide and aminopeptidase b2324 protein are not in contact after expression, contacting the uncleaved polypeptide with the aminopeptidase b2324 protein so as to produce the cleaved polypeptide.

Preferably, the polypeptide is heterologous to the cells, and more preferably is one of the polypeptides in the categories given above. Preferably, the type of cell is selected from those set forth above, except without the yfcK gene deleted. The yfcK gene can be introduced as by a vector or can be endogenous to the host cell, and is preferably overexpressed relative to expression of the nucleic acid encoding the polypeptide so as to favor the enzymatic cleavage reaction.

In another preferred aspect, the uncleaved polypeptide is recovered from the cells before contact with the aminopeptidase b2324 protein. In the recovery, preferably, the cells are disrupted (using techniques as set forth above) and then lysed. After lysis the uncleaved polypeptide is preferably incubated with the aminopeptidase b2324 protein so as to clip off the amino terminus, and the cleaved polypeptide is purified from the incubated lysate. Preferably the lysate is incubated for at least about 1 hour at about 20-40° C., more preferably for about 2-50 hours at about 30-40° C.

I. Production and Recovery of Uncleaved Polypeptide

A. Insertion of Nucleic Acid into a Replicable Vector

The nucleic acid encoding the polypeptide of interest is suitably cDNA or genomic DNA from any source, provided it encodes the polypeptide(s) of interest.

The heterologous nucleic acid (e.g., cDNA or genomic DNA) is suitably inserted into a replicable vector for expression in the bacterium under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with *E. coli* hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the *E. coli* host for expression of the selectable marker genes.

(i) Signal Sequence Component

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell.

For bacterial host cells that do not recognize and process the native or a eukaryotic polypeptide signal sequence, the signal sequence is substituted by a suitable prokaryotic signal sequence selected, for example, from the group consisting of the alkaline phosphatase, penicillinase, 1 pp, or heat-stable enterotoxin II leaders.

(ii) Origin of Replication Component

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria such as *E. coli*.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for *Bacilli*.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)), or hygromycin (Sugden et al., *Mol. Cell. Biol.*, 5: 410-413 (1985)). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the polypeptide of interest contains a suitable promoter that is recognized by the host organism and is operably linked to the nucleic acid encoding the polypeptide of interest. Promoters suitable for use with prokaryotic hosts include the beta-lactamase and lactose promoter systems (Chang et al., *Nature*, 275: 615 (1978); Goeddel et al., *Nature*, 281: 544 (1979)), the arabinose promoter system (Guzman et al., *J. Bacteriol.*, 174: 7716-7728 (1992)), alkaline phosphatase, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21-25 (1983)). However, other known bacterial promoters are suitable. Their nucleotide sequences have been published, thereby enabling a skilled worker operably to ligate them to DNA encoding the polypeptide of interest (Siebenlist et al., *Cell*, 20: 269 (1980)) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

(v) Construction and Analysis of Vectors

Construction of suitable vectors containing one or more of the above listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA*, 74: 5463-5467 (1977) or Messing et al., *Nucleic Acids Res.*, 9: 309 (1981), or by the method of Maxam et al., *Methods in Enzymology*, 65: 499 (1980).

B. Selection and Transformation of Host Cells

As defined above, many types of gram-negative bacterial cells can be used for purposes of having a deficient yfcK gene, and those mentioned above are examples of such. *E. coli* strain W3110 is a preferred parental strain because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such *E. coli* hosts, along with their genotypes, being included in the table below:

| Strain | Genotype |
|---|---|
| W3110 | K-12 F lambda$^-$IN(rrnD-rrnE)1 |
| 1A2 | W3110 ΔfhuA or W3110 tonAΔ |
| 7C1 | W3110 ΔfhuA Δ(arg-F-lac)169 phoAΔE15 |
| 9E4 | W3110 ΔfhuA ptr3 |
| 16C9 | W3110 ΔfhuA Δ(arg-F-lac)169 phoAΔE15 deoC2 |
| 23E3 | W3110 ΔfhuA Δ(arg-F-lac)169 phoAΔE15 deoC2 degP::kanR |
| 27A7 | W3110 ΔfhuA ptr3 phiΔE15 Δ(argF-lac)169 |
| 27C6 | W3110 ΔfhuA ptr3 phoAΔE15 Δ(argF-lac)169 ΔompT |
| 27C7 | W3110 ΔfhuA ptr3 phoAΔE15 Δ(argF-lac)169 ΔompT degP41 (ΔpstI-kan$^R$) |
| 33B6 | W3110 ΔfhuA Δ(arg-F-lac)169 phoAΔE15 deoC2 degP::kanR ilvG2096 |
| 33D3 | W3110 ΔfhuA ptr3 lacIq lacL8 ΔompT degP41 (ΔpstI-kan$^R$) |
| 36F8 | W3110 ΔfhuA phoAΔE15 Δ(argF-lac)169 ptr3 degP41 (ΔpstI-kan$^R$) ilvG2096$^R$ |
| 37D6 | W3110 tonAΔ ptr3 phoAΔE15 Δ(argF-lac)169 ompTΔ degP41kan$^r$ rbs7Δ ilvG |
| 40B4 | Strain 37D6 with a non-kanamycin resistant degP deletion mutation |
| 40G3 | W3110 tonAΔ phoAΔE15 Δ(argF-lac)169 deoC ΔompT degP41 (ΔPstI-kan$^r$) ilvG2096$^R$ phn(EcoB) |
| 43D3 | W3110 ΔfhuA ptr3 phoAΔE15 Δ(argF-lac)169 ΔompT degP41 (ΔPst1-kan$^R$) ilvG2096$^R$ |
| 43E7 | W3110 ΔfhuA Δ(argF-lac)169 ΔompT ptr3 phoAΔE15 degP41 (ΔPst1-kan$^S$) ilvG2096$^R$ |
| 44D6 | W3110 ΔfhuA ptr3 Δ(argF-lac)169 degP41 (Δpst1- kan$^S$) ΔompT ilvG2096$^R$ |
| 45F8 | W3110 ΔfhuA ptr3 Δ(argF-lac)169 degP41 (Δpst1- kan$^S$) ΔompT phoS* (T10Y) ilvG2096$^R$ |
| 45F9 | W3110 ΔfhuA ptr3 Δ(argF-lac)169 degP41 (Δpst1- kan$^S$) ΔompT ilvG2096$^R$ phoS* (T10Y) Δcyo::kan$^R$ |

Also suitable are the intermediates in making strain 36F8, i.e., 27B4 (U.S. Pat. No. 5,304,472) and 35E7 (a spontaneous temperature-resistant colony isolate growing better than 27B4). An additional suitable strain is the *E. coli* strain having the mutant periplasmic protease(s) disclosed in U.S. Pat. No. 4,946,783 issued Aug. 7, 1990.

The mutant cell of this invention may be produced by chromosomal integration of the yfcK gene into the parental cell or by other techniques, including those set forth in the Examples below.

The nucleic acid encoding the polypeptide is inserted into the host cells. The nucleic acid is introduced into the appropriate bacterial cell using any suitable method, including transformation by a vector encoding the polypeptide. Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for prokaryotic cells or other cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

An example of transformation by insertion of the gene encoding the polypeptide into the *E. coli* host genome involves including in the vector for transformation a DNA sequence that is complementary to a sequence found in *E. coli* genomic DNA. Transfection of *E. coli* with this vector results in homologous recombination with the genome and insertion of the gene encoding the polypeptide. Preferably, the nucleic acid is inserted by transforming the host cells with the above-described expression vectors and culturing in conventional nutrient media modified as appropriate for inducing the various promoters.

C. Culturing the Host Cells

Bacterial cells used to produce the polypeptide of interest of this invention are cultured in suitable media as described generally, e.g., in Sambrook et al., supra.

For secretion of an expressed or over-expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

Where the alkaline phosphatase promoter is employed, *E. coli* cells used to produce the polypeptide of interest of this invention are cultured in suitable media in which the alkaline phosphatase promoter can be partially or completely induced as described generally, e.g., in Sambrook et al., supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

Any other necessary media ingredients besides carbon, nitrogen, and inorganic phosphate sources may also be included at appropriate concentrations introduced alone or as a mixture with another ingredient or medium such as a complex nitrogen source. The pH of the medium may be any pH from about 5-9, depending mainly on the host organism.

If the promoter is an inducible promoter, for induction to occur, typically the cells are cultured until a certain optical density is achieved, e.g., a $A_{550}$ of about 200 using a high cell density process, at which point induction is initiated (e.g., by addition of an inducer, by depletion of a medium component, etc.), to induce expression of the nucleic acid encoding the polypeptide of interest.

D. Detecting Expression

Nucleic acid expression may be measured in a sample directly, for example, by conventional Southern blotting, northern blotting to quantitate the transcription of mRNA (Thomas, *Proc. Natl. Acad. Sci. USA*, 77: 5201-5205 (1980)), dot blotting (DNA analysis), or in situ hybridization, using an appropriately labeled probe, based on the sequences of the polypeptide. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, assays or gels may be employed for detection of protein.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells. Moreover, when antibodies reactive against a given gene product are available, such antibodies can be used to detect the gene product in any known immunological assay (e.g., as in Harlowe et al., *Antibodies: A Laboratory Manual*, Cold Spring Harbor Laboratory Press, New York, 1988).

The secreted gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^{3}H$), carbon-14 ($^{14}C$), sulfur-35 ($^{35}S$), and the like. For example, the host cell can be grown in $^{35}S$-methionine or $^{35}S$-cysteine medium, and a significant amount of the $^{35}S$ label will be preferentially incorporated into any newly synthesized polypeptide, including the over-expressed heterologous polypeptide. The $^{35}S$-containing culture medium is then removed and the cells are washed and placed in fresh non-radioactive culture medium. After the cells are maintained in the fresh medium for a time and under conditions sufficient to allow secretion of the $^{35}S$-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are provided in Goeddel, D. V. (ed.) 1990, Gene Expression Technology, *Methods in Enzymology*, Vol. 185 (Academic Press), and Sambrook et al., supra.

E. Recovery/Purification

After the polypeptide is produced it may be recovered from the cell by any appropriate means that depend, for example, on from which part of the cell the recovery is. The polypeptide may be recovered from the cytoplasm, periplasm, or cell culture media. The polypeptide of interest is preferably recovered from the periplasm or culture medium as a secreted polypeptide. The polypeptide of interest is purified from recombinant cell proteins or polypeptides to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and refolded, if necessary, and is purified from contaminant soluble proteins and polypeptides. Any typical step to remove the cleaved polypeptide impurity from the mixture is eliminated from the purification scheme because the aminopeptidase is no longer present. In one preferred embodiment, the aggregated polypeptide is isolated, followed by a simultaneous solubilization and refolding step, as disclosed in U.S. Pat. No. 5,288,931.

In a particularly preferred embodiment, the recovery is from the periplasm by cell disruption (by techniques as set forth above) to form a lysate, followed by purification of intact, uncleaved polypeptide from the lysate. Preferably, the lysate is incubated before purification. More preferably, the lysate is incubated for at least about 1 hour at about 20-25° C., still more preferably for about 2-50 hours at about room temperature, still more preferably about 5-45 hours at about room temperature, and most preferably for about 20-30 hours at about room temperature.

The following procedures are exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; and gel filtration using, for example, SEPHADEX G-75™ columns.

II. Production and Recovery of Cleaved Polypeptide

In this alternative process, the polypeptide is contacted with the aminopeptidase b2323 polypeptide directly so that it is clipped. This may be accomplished by several means, including incubation therewith at about 20-40° C., preferably about 30-40° C., for a time ranging up to about 50 hours, preferably at least about 1 hour to 45 hours. In a preferred aspect of this contacting method, the invention provides a method of producing a cleaved polypeptide comprising culturing bacteria cells harboring a yfcK gene and comprising nucleic acid encoding the corresponding uncleaved polypeptide that has an added amino acid at its N-terminus. The culturing is under conditions so as to express or overexpress the yfcK gene and to express the nucleic acid encoding the uncleaved polypeptide, and if the uncleaved polypeptide and aminopeptidase b2324 protein are not in contact after expression, contacting the uncleaved polypeptide with the aminopeptidase b2324 protein so as to produce the cleaved polypeptide. Preferably the contacting is by incubation under the conditions set forth above or below and the culturing occurs in a fermentor.

In a preferred aspect the polypeptide is heterologous to the cells, more preferably a eukaryotic polypeptide, and still more preferably a mammalian, especially human, polypeptide. The preferred cell is a *Salmonella* or *Enterobacteriaceae* cell, still more preferably an *E. coli* cell, and most especially W3110. Also preferred is a cell that is deficient in at least one gene encoding a protease, such as degP or fhuA or both.

In a preferred aspect the culturing conditions are such that the yfcK gene is overexpressed. The yfcK gene may be native to the bacteria cells or introduced thereto, as by transformation with a vector harboring such gene.

In another preferred aspect the uncleaved polypeptide is recovered from the cells before contact with the aminopeptidase b2324 protein, and the uncleaved polypeptide is recovered from the periplasm or culture medium of the cell. In one embodiment the recovery is by cell disruption (as described above) to form a lysate, the aminopeptidase is added, and then the cleaved polypeptide is purified from the lysate. Preferably in this instance the lysate is incubated with the aminopeptidase before the purification step. More preferably, the lysate is incubated for at least about 1 hour at about 20-40° C., still more preferably for about 2-50 hours at about 30-40° C., still more preferably about 5-45 hours at about 30-40° C., and most preferably for about 20-30 hours at about 35-38° C. before the purification step.

Where cleaved polypeptides are prepared recombinantly, the parental strains, culturing conditions, detection of expression, recovery/purification, and basic techniques are generally as set forth above. However, for overexpression in the strain to be cultured, typically the yfcK gene, whether endogenous (in the chromosome) or exogenous to the host cell, is operably linked to an inducible promoter so that the gene can be overexpressed when the promoter is induced. The culturing preferably takes place under conditions whereby expression of the yfcK gene is induced prior to induction of the expression of the nucleic acid encoding the polypeptide. Suitable techniques for overexpression of genes useful herein include those described by Joly et al., *Proc. Natl. Acad. Sci. USA*, 95, 2773-2777 (1998); U.S. Pat. Nos. 5,789,199 and 5,639,635; Knappik et al., *Bio/Technology*, 11(1):77-83 (1993); and Wulfing and Pluckthun, *Journal of Molecular Biology*, 242(5):655-69 (1994).

The invention will be more fully understood by reference to the following examples. They should not, however, be construed as limiting the scope of the invention. All literature and patent citations herein are incorporated by reference.

EXAMPLE 1

Materials and Methods

DNA sequences were PCR-amplified upstream and downstream of the yfcK gene encoding b2324 identified by the genomic sequencing project (GenBank listing resulting from Blattner et al., supra). Then these fused sequences were recombined on the chromosome of a W3110 strain by P1 transduction and screened by PCR for deletions (Metcalf et al., *Gene*, 138: 1-7 (1994)) to produce strain 61G3, which has the genotype W3110 ΔfhuA Δ(arg-F-lac)169 phoAΔE15 deoC2 degP::kanR ilvG2096 ΔyfcK.

Specifically, this strain was constructed in several steps using techniques involving transduction with phage P1kc, derived from P1 (J. Miller, *Experiments in Molecular Genetics*, Cold Spring Harbor, N.Y., Cold Spring Harbor Laboratory, 1972) and transposon genetics (Kleckner et al., *J. Mol. Biol.*, 116: 125-159 (1977)). The starting host used was *E. coli* K-12 W3110, which is a K-12 strain that is F-lambda-(Bachmann, *Bact. Rev.*, 36: 525-557 (1972); Bachmann, "Derivations and Genotypes of Some Mutant Derivatives of *Escherichia coli* K-12," p. 1190-1219, in F. C. Neidhardt et al., ed., *Escherichia coli and Salmonella typhimurium: Cellular and Molecular Biology*, vol. 2, American Society for Microbiology, Washington, D.C., 1987). Introduction of the tonA (fhuA) mutation into the genome is described in detail in U.S. Pat. No. 5,304,472 issued Apr. 19, 1994. The Tn10 insertion in the ilv gene was introduced by P1 transduction. The isoleucine/valine auxotrophy was transduced to prototrophy using P1 phage grown on a strain carrying the ilvG2096$^R$ mutation (Lawther et al., *Proc. Natl. Acad. Sci. USA*, 78: 922-925 (1981)), which repairs a frameshift that causes the wild-type *E. coli* K-12 to be sensitive to valine. The degP41 kan$^r$ mutation is described in U.S. Pat. No. 5,304,472. The ilvG2096$^R$ locus can be confirmed by the resistance of the 33B6 host to 40 μg/mL valine (0.3 mM). Two deletion mutations, phoAΔE15 and Δ(argF-lac)169, are described in U.S. Pat. No. 5,304,472. The deoC2 mutation is described in Mark et al., *Mol. Gen. Genet.* 155: 145-152 (1977). The complete derivation of the strain 61G3 is shown in FIG. 1.

This strain was then transformed with an expression plasmid designated hGH4R that expresses and secretes hGH (with the N-terminal phenylalanine) in both shake-flask and 10-L fermentations. The construction of phGH4R is detailed in Chang et al., *Gene,* 55: 189-196 (1987). This transformation resulted in the strain JJGH1. The cells were cultured as described in Andersen et al., *Biotechnology and Bioengineering,* 75(2), 212-218 (2001). A crude lysate was made by sonicating the cells after hGH was produced and the lysate was incubated at 37° C. for 0 to 24 hours and at room temperature for 0 to 42 hours. Use of the higher temperature was to improve the ability to detect des-phe and des-phe-pro hGH by the assay method, but is not preferred for purification of hGH. Normally hGH purification is done in the cold to dampen the amount of these clipped forms.

The same experiment was performed using as control a parent strain (16C9 with genotype W3110 ΔfhuA Δ(arg-F-lac)169 phoAΔE15 deoC2) transformed with phGH4R. This strain is suitable for this purpose, as the degP and ilvG mutations in strain 61G3 have no effect on aminopeptidase activity.

The control and experimental samples were then centrifuged to remove particulates and the soluble phases were analyzed by LC-MS (liquid chromatography, mass spectrometry analysis). The masses for intact, des-phe, and des-phe-pro forms of hGH were monitored.

Results

FIGS. 2 and 4 show respectively the results for room temperature and 37° C. incubations with the control strain (16C9/phGH4R), and FIGS. 3 and 5 show respectively the results for room temperature and 37° C. incubations with JJGH1, which has the aminopeptidase knocked out. The actual numbers for the four figures are shown in Table 1 below (under Temp=37° C. and Temp=RT). It can be seen that there are virtually no phenylalanine-cleaved impurities after 15 hours of incubation at 37° C., and even with no incubation there is a lessening of the amount of the impurities. It can also be seen that even at room temperature incubation, the amount of the mutant polypeptide with missing N-terminal phenylalanine is reduced with the JJGH1 cell line as compared to the control at all times of incubation. Purification of the intact polypeptide can be readily carried out by conventional or known chromatography means.

TABLE 1

| Sample | Time | Area | | | Area % | | |
|---|---|---|---|---|---|---|---|
| | | des-phe | Native | des-phe-pro | des-phe | Native | des-phe-pro |
| Temp = 37° C. | | | | | | | |
| Control | 0 | 16159.80 | 4486460.00 | 19642.70 | 0.36 | 99.21 | 0.43 |
| JJGH1 | 0 | 11927.90 | 3376380.00 | 7637.14 | 0.35 | 99.42 | 0.22 |
| Control | 15 | 14372.30 | 1097210.00 | 976760.00 | 46.77 | 52.53 | 0.69 |
| JJGH1 | 15 | 27163.70 | 2674010.00 | 16357.80 | 1.00 | 98.40 | 0.60 |
| Control | 24 | 1058950.00 | 839418.00 | 17580.50 | 55.27 | 43.81 | 0.92 |
| JJGH1 | 24 | 29409.90 | 2306690.00 | 11999.30 | 1.25 | 98.23 | 0.51 |
| Temp = RT | | | | | | | |
| Control | 0 | 16159.80 | 4486460.00 | 19642.70 | 0.36 | 99.21 | 0.43 |
| JJGH1 | 0 | 11927.90 | 3376380.00 | 7637.14 | 0.35 | 99.42 | 0.22 |
| Control | 15 | 46158.20 | 364234.00 | 7950.57 | 1.24 | 98.53 | 0.21 |
| JJGH1 | 15 | 183740.00 | 19431400.00 | 39130.00 | 0.94 | 99.06 | 0.20 |
| Control | 24 | 100774.00 | 4561070.00 | 19501.10 | 2.15 | 97.43 | 0.42 |
| JJGH1 | 24 | 160737.00 | 19711600.00 | 98221.60 | 0.80 | 98.70 | 0.49 |
| Control | 42 | 122177.00 | 3933770.00 | 19246.40 | 3.00 | 96.53 | 0.47 |
| JJGH1 | 42 | 213143.00 | 18242500.00 | 91090.90 | 1.15 | 98.36 | 0.49 |

The results show that a ΔyfcK strain can be used to prevent N-terminal cleavage of polypeptides.

What is claimed is:

1. A method of producing a cleaved, polypeptide comprising culturing gram-negative bacterial host cells harboring
   (a) an endogenous or heterologous nucleic acid encoding an aminopeptidase having at least 95% sequence identity to the aminopeptidase b2324 set forth by amino acid residues 1 to 688 of SEQ ID NO:2 and
   (b) a heterologous nucleic acid encoding the corresponding uncleaved polypeptide that has an added amino acid at its N-terminus,
   wherein the culturing is under conditions
       (i) so as to express or overexpress the aminopeptidase encoded by the nucleic acid of (a),
       (ii) so as to express the uncleaved polypeptide encoded by (b), and
       (iii) wherein the uncleaved polypeptide and aminopeptidase are in contact after expression, so as to produce the cleaved polypeptide.

2. A method of producing a cleaved polypeptide comprising culturing gram-negative bacterial host cells harboring
   (a) an endogenous or heterologous nucleic acid having at least 95% sequence identity to the yfcK gene set forth by nucleotides 1 to 2067 of SEQ ID NO:1 and encoding an aminopeptidase and
   (b) a nucleic acid encoding the corresponding uncleaved polypeptide that has an added amino acid at its N-terminus
   wherein the culturing is under conditions
       (i) so as to express or overexpress the aminopeptidase encoded by the nucleic acid of (a),
       (ii) so as to express the uncleaved polypeptide encoded by (b), and
       (iii) wherein the uncleaved polypeptide and aminopeptidase are in contact after expression, so as to produce the cleaved polypeptide.

3. The method of claim 1 or 2 wherein the cleaved polypeptide is a mammalian polypeptide.

4. The method of claim 1 or 2 wherein the cell is deficient in at least one gene encoding a protease.

5. The method of claim 1 or 2 wherein the culturing conditions are such that the nucleic acid encoding the aminopeptidase is overexpressed.

6. The method of claim 1 or 2 wherein the culturing takes place in a fermentor.

7. The method of claim 2 or 4 wherein the cleaved polypeptide is recovered from the periplasm or culture medium of the cell.

8. The method of claim 7 wherein the recovery is by cell disruption to form a lysate and wherein the cleaved polypeptide is purified from the lysate.

9. The method of claim 8 wherein the lysate is incubated before the purification step.

10. The method of claim 9 wherein the lysate is incubated for at least about 1 hour at about 20-40° C.

11. The method of claim 1 or 2 wherein the host cell is selected from the group consisting of: *Enterobaceriaceae, Azotobacter, Pseudomonas, Rhizobia, Vitreoscill* and *Paracoccus*.

12. The method of claim 11, wherein the host cell is *Enterobacteriaceae*.

13. The method of claim 12, wherein the host cell is an *Enterobacteriaceae* selected from the group consisting of: *Escherichia, Enterobacter, Erwinia, Kiebsiella, Proteus, Salmonella, Serratia* and *Shigella*.

14. The method of claim 12, where the host cell is *E. coli*.

15. The method of claim 14, wherein the host cell an *E. coli* selected from the group consisting of strains W3110 (ATCC 27,325), 294 (ATCC 31,446) and X1776 (ATCC 31,537).

16. The method of claim 15, wherein the host cell is *E. coli* strain W3110 (ATCC 27,325).

17. The method of claim 15, wherein the host cell is *E. coli* strain 294 (ATCC 31,446).

18. The method of claim 1, wherein the sequence identity is 100%.

19. The method of claim 2, wherein the sequence identity is 100%.

* * * * *